United States Patent
Badger et al.

(10) Patent No.: US 6,334,395 B1
(45) Date of Patent: *Jan. 1, 2002

(54) METHODS, APPARATUS, AND SYSTEMS FOR ACCELERATED BIOREMEDIATION OF EXPLOSIVES

(75) Inventors: Farrell G. Badger, Mapleton, UT (US); Brendan M. Welch, Farmington, CT (US); Ronald D. Thomas, Woodlands Hills, UT (US); Lyman G. Bahr, Payson, UT (US); Dean F. Richards, Pleasant Grove, UT (US)

(73) Assignee: The Ensign-Bickford Company, Simsbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/866,205

(22) Filed: May 30, 1997

Related U.S. Application Data

(63) Continuation-in-part of application No. 08/743,460, filed on Oct. 18, 1996, now Pat. No. 6,120,627, which is a continuation-in-part of application No. 08/658,104, filed on Jun. 4, 1996, now abandoned, and a continuation-in-part of application No. 08/560,074, filed on Nov. 17, 1995, now abandoned, which is a continuation-in-part of application No. 08/687,092, filed on Jun. 4, 1996, now abandoned, which is a continuation-in-part of application No. 08/560,102, filed on Nov. 17, 1995, now abandoned.

(51) Int. Cl.[7] .............................. F42B 3/00; A62D 3/00
(52) U.S. Cl. ..................... 102/293; 588/203; 149/24
(58) Field of Search ................... 588/203; 149/24; 102/293

(56) References Cited

U.S. PATENT DOCUMENTS

| | | | |
|---|---|---|---|
| 2,330,110 A | 9/1943 | Buchan | 166/21 |
| 3,157,119 A | 11/1964 | Porter | 102/21.8 |
| 3,710,718 A | 1/1973 | Grant | 102/23 |
| 4,016,117 A | 4/1977 | Griffin | 260/17.4 |
| 4,064,941 A | 12/1977 | Smith | 166/300 |

(List continued on next page.)

OTHER PUBLICATIONS

Boopathy, R. et al. Biological Transformation of 2.4.6–Trinitrotoluene (TNT) by Soil Bacteria Isolated from TNT–Contaminated Soil. 47 Bioresource Technology 19 (1994).

Boopathy, R. et al., Biotransformation of 2.4.6–Trinitrotoluene (TNT) by Co–Metabolism with Various Co–Substrates: A Laboratory–Scale Study, 47 Bioresource Technology 205 (1994).

Kaplan, David L., Biotechnology and Bioremediation for Organic Energetic Compounds, Organic Energetic Compunds, 373–416 (Marinkas, Paul L. ed. 1944).

(List continued on next page.)

Primary Examiner—Peter A. Nelson
(74) Attorney, Agent, or Firm—TraskBritt

(57) ABSTRACT

Technology for in situ remediation of undetonated explosive material. An explosive apparatus contains an explosive material in close proximity with a carrier containing microorganisms. An explosive mixture capable of self remediation includes an explosive material that is intermixed with or lies proximate to the carrier. The microorganisms are either mobile or temporarily deactivated by freeze drying until rehydrated and remobilized. The microorganisms are capable of metabolizing the explosive material. Examples of such microorganisms include Pseudomonas spp., Escherichia spp., Morganella spp., Rhodococcus spp., Comamonas spp., and denitrifying microorganisms. If the explosive material fails to detonate, the explosive is remediated by the action of the microorganisms. Remediation includes both disabling of the explosive material and detoxification of the resulting chemical compositions.

45 Claims, 13 Drawing Sheets

U.S. PATENT DOCUMENTS

Figure 1:
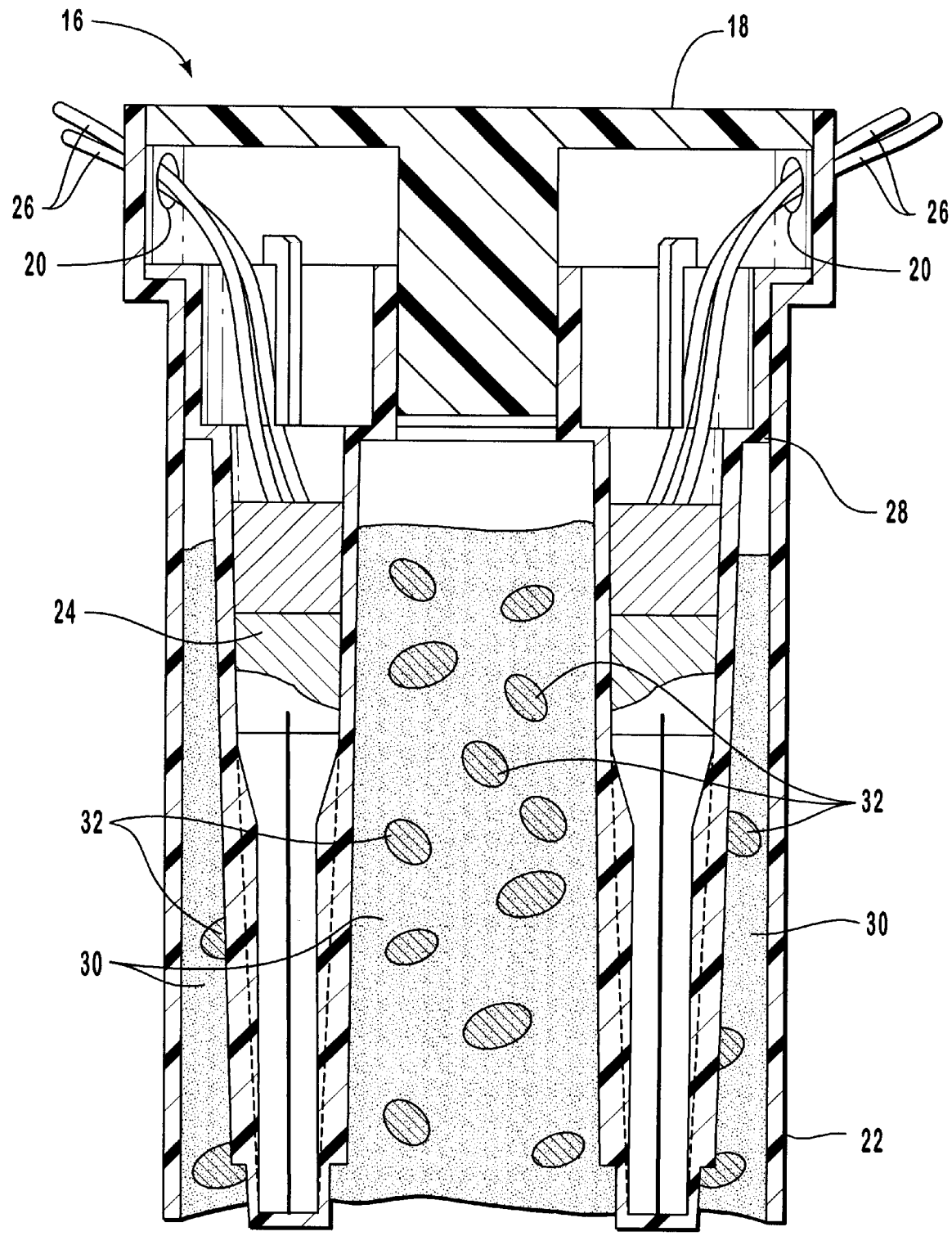

| | | | |
|---|---|---|---|
| 4,108,728 A | 8/1978 | Spinner et al. | 195/127 |
| 4,351,729 A | 9/1982 | Witt | 210/603 |
| 4,365,557 A | 12/1982 | Couture et al. | 102/341 |
| 4,845,034 A | 7/1989 | Menger et al. | 435/167 |
| 4,929,552 A | 5/1990 | Gold et al. | 435/128 |
| 4,961,381 A | 10/1990 | McLaughlin | 102/319 |
| 5,011,614 A | 4/1991 | Gresser et al. | 210/761 |
| 5,085,998 A * | 2/1992 | Lebron et al. | 435/262 |
| 5,120,441 A | 6/1992 | Jackson et al. | 210/602 |
| 5,139,365 A | 8/1992 | Chesner | 405/129 |
| 5,139,726 * | 8/1992 | Chazono et al. | 424/92 |
| 5,296,146 A | 3/1994 | Jackson et al. | 210/602 |
| 5,302,285 A * | 4/1994 | Attaway et al. | 210/605 |
| 5,314,821 A | 5/1994 | Tyndall | 435/252.1 |
| 5,370,845 A | 12/1994 | Miller et al. | 422/186.3 |
| 5,387,271 A | 2/1995 | Crawford et al. | 71/9 |
| 5,392,860 A | 2/1995 | Ross | 166/376 |
| 5,414,198 A * | 5/1995 | Brodman et al. | 149/124 X |
| 5,420,035 A | 5/1995 | Tyndall | 435/252.1 |
| 5,449,618 A * | 9/1995 | Tyndall et al. | 588/203 X |
| 5,455,173 A | 10/1995 | Crawford et al. | 435/264 |
| 5,478,743 A | 12/1995 | Perkins et al. | 435/262.5 |
| 5,484,730 A | 1/1996 | Tyndall et al. | 435/264 |
| 5,511,482 A | 4/1996 | DiPietropolo | 102/426 |
| 5,518,919 A | 5/1996 | Tyndall | 435/262.5 |
| 5,543,324 A | 8/1996 | Rajan | 435/252.4 |
| 5,578,488 A | 11/1996 | Tyndall et al. | 435/262.5 |
| 5,610,062 A | 3/1997 | Tyndall | 435/252.4 |
| 5,616,162 A | 4/1997 | Crawford et al. | 71/9 |
| 5,736,669 A * | 4/1998 | Thomas et al. | 102/293 |
| 5,763,736 A | 6/1998 | Daume | 588/203 |
| 5,763,815 A * | 6/1998 | Thomas et al. | 102/293 |
| 5,814,514 A * | 9/1998 | Steffan et al. | 435/262 |
| 6,120,627 A | 9/2000 | Badger et al. | 149/108.8 |

OTHER PUBLICATIONS

Knezovich, John P. et al., *Chemical and Biological Systems for Treating Waste Streams Contaminated with High Explosives*, paper submitted for JANNAF Safety and Environmental Protection Subcommittee Meeting in Tampa, Florida (Dec. 5–8, 1995).

Knezovich, John P. et al., *Chemical and Biological Systems for Regenerating Activated Carbon Contaminated with High Explosives*, paper submitted to Proceedings Demin '94 in Luxembourg, Luxembourg (Nov. 14–16, 1994).

* cited by examiner

METHODS, APPARATUS, AND SYSTEMS FOR ACCELERATED BIOREMEDIATION OF EXPLOSIVES

RELATED APPLICATIONS

This application is a continuation-in-part application of U.S. patent application Ser. No. 08/743,460, filed Oct. 18, 1996 and now U.S. Pat. No. 6,120,627, which is a continuation-in-part of both U.S. patent application Ser. No. 08/658,104, filed on Jun. 4, 1996 and now abandoned, which is a continuation-in-part of U.S. patent application Ser. No. 08/560,074, filed on Nov. 17, 1995 and now abandoned, and U.S. patent application Ser. No. 08/687,092, filed Jun. 4, 1996 and now abandoned, which is a continuation-in-part application of U.S. patent application Ser. No. 08/560,102, filed on Nov. 17, 1995 and now abandoned.

The present application discloses subject matter related to that disclosed in U.S. patent application Ser. No. 08/658,995 and in U.S. patent application Ser. No., 08/658,142 both filed Jun. 4, 1996 now U.S. Pat. No. 5,736,569, As continuation-in-part application of U.S. patent application Ser. No. 08/560,074, filed on Nov. 17, 1995 and now abandoned.

BACKGROUND OF THE INVENTION

1. The Field of the Invention

The present invention is directed to systems, apparatus, and methods for remediating explosives. More particularly, the present invention is directed to the remediation of explosives which have not detonated.

2. Background Art

Explosive charges are inherently dangerous in a number of respects. Inadvertent detonation poses risks of severe personal injury or death, as well as of substantial property destruction and consequential losses. Explosive charges are, in addition, comprised of material substances, which even when not consolidated in a shape capable of performing as a detonatable explosive charge, may be toxic and thus potentially injurious to human health and to complex as well as simple plant and animal life.

Explosive charges that are not securely stored in a supervised manner, or isolated from the environment and from indiscriminate access by human and animal life forms, thus present both safety and environmental hazards.

Such hazards are pointedly apparent where an explosive charge fails to detonate after the explosive charge has been installed for that purpose during activities pertaining to mining, construction, or to seismic surveying. Fortunately, installed explosive charges that do not detonate as planned are usually locatable and often recoverable through the expenditure of reasonable efforts and without safety risks to personnel. On the other hand, there do routinely arise circumstances in which undetonated explosive charges of this type are not recovered or simply cannot be recovered. In such circumstances, there exists a risks that the undetonated explosive charge could at some subsequent time be detonated inadvertently or become a source of potentially harmful contaminants.

As an example, seismic survey data used to ascertain the nature of subsurface ground structures is routinely obtained by recording and analyzing shock waves that are propagated into the ground and produced by detonating explosive charges. The shock waves are then monitored during transmission through the ground. In this role, such seismic charges are usually utilized in large sets, installed as an array of individual seismic charges at widely disbursed locations. The seismic charges are interconnected with detonation equipment for remote detonation, either simultaneously or in sequence.

Seismic charges for such surveys can be detonated either above or below the surface of the ground. In either case, it is not uncommon that at least one of any set of such seismic charges does not detonate as intended. Such failures may be caused by defects in the explosive charge itself, by damage caused during installation, by faulty detonation equipment, or by the failure of personnel in the field to make effective interconnections between that detonation equipment and each seismic charge in the installed set.

When a seismic charge installed above the ground fails to detonate as intended, it is usually possible to locate and safely recover the undetonated seismic charge. Nonetheless, circumstances do exist where the detonation of a set of seismic charges installed above the ground dislocates one of the undetonated seismic charges in the set, directing that undetonated seismic charge into a terrain in which the charge cannot be located or cannot be recovered easily. Responsible seismic crews naturally are trained to exercise all reasonable efforts to recover undetonated seismic charges that are located on the surface of the ground, but even the most rigorously indoctrinated and enthusiastic seismic personnel cannot guarantee that all undetonated seismic charges installed above the ground are ultimately recovered.

Aside from the human factor involved, the intervention of severe weather conditions, such as sandstorms, blizzards, tornadoes, or hurricanes, can impede efforts to recover undetonated seismic explosives. Some such weather conditions offer the prospect of even altering the terrain, thereby burying the undetonated seismic charge temporarily or for a substantial duration. Floods can cover the seismic survey site, removing or obscuring undetonated seismic charges. In the extreme, geological surface changes, such as mudslides, rockfalls, and fissures caused by earthquakes, by heavy weather, or even by seismic survey activity itself, can preclude the recovery of undetonated seismic charges, and even obscure the understanding that any seismic charge has failed to detonate.

The safety risks and environmental hazards posed by loose, undetonated explosive charges will be present where any undetonated seismic charge remains unrecovered after the detonation of the set of seismic charges of which it was a part.

The likelihood that an undetonated seismic charge will be abandoned is greatest, however, relative to the conduct of seismic survey activity based on the detonation of seismic charges installed below the surface of the ground. In such sub-surface seismic detonation activity, a series of deep boreholes are drilled into the earth or rock at predetermined locations that are intended to maximize the data to be derived from the shock waves promulgated from the detonation of the seismic charges. A seismic charge is placed at the bottom of each borehole and then shut in the borehole in a relatively permanent manner using a concrete or a sealing compound, such as bentonite. The balance of the borehole is then backfilled with loose soil and rock, a process which alone accounts for the majority of failed seismic detonations. Backfill materials have an understandable tendency to break the detonating cord leg wires or non-electric transmission line that interconnects the installed seismic charge at the bottom of the borehole with detonating equipment located above the ground. If a seismic charge installed below the ground fails to detonate, the easy removal of the undetonated seismic charge is seriously impeded by yards of backfill and the cured concrete or sealing compound in which the seismic charge was embedded at the bottom of the original borehole. Removing such an installed seismic charge by reexcavating the original borehole or by digging around the original borehole to avoid the sealing compound is extremely laborious and time consuming, potentially unsafe, and in many circumstances virtually impossible.

Thus, in conducting seismic survey activities, particularly seismic survey activities involving the detonation of seismic charges below the surface of the ground, undetonated seismic charges are regularly abandoned in the field. Frequently, even the precise location of undetonated seismic charges cannot be pinpointed. The risks from undetonated explosive charges installed in the ground endure for a substantial time, usually exceeding the durability of ground surface warning signs, fencing, or the continued possession and control of access to the site by an original owner. Eventually, the pressure of human population growth may render the site attractive for civil or industrial activities that would not be consistent with buried undetonated explosive charges.

The associated dangers include first that of an accidental detonation at some future time. Less dramatic, but certainly of longer duration, are risks presented by the material substance of those undetonated charges. Once released from the confines of the casing of an explosive assembly, the explosive material therein may cease to present any risk of explosion. This type of release of explosive materials can occur through corrosion of the casing through the action of ground water, the fracture of the casing during careless installation, or the shifting of the ground structure at the location at which the undetonated seismic charge was abandoned. In due course, the prolonged effect of these forces in combination with surface erosion or subsurface fluid migration can disburse over a large area the material of a fractured explosive charge. That material may constitute a potentially problematic contaminant. Even if detected, remedial activities may be required to contain and possibly eliminate the contaminant.

Nonetheless, no practical methods exist for reliably remediating the risks posed by undetonated explosive charges, particularly where those undetonated explosive charges are originally installed below the surface of the ground.

SUMMARY OF THE INVENTION

It is thus the broad object of the present invention to protect public health and safety from risks arising from incidents of abandoned undetonated explosive charges.

Accordingly, it is a related object of the present invention to eliminate the possibility of detonation of abandoned explosive charges.

It is a complementary object of the present invention to reduce the likelihood that abandoned undetonated explosive charges will contribute to environmental pollution.

Thus, it is a specific object of the present invention to provide apparatus, systems, and methods for remediating in situ any installed explosive charge that fails to detonate as intended.

It is a particular object of the present invention to provide such apparatus, systems, and methods as are capable of reliably and safely remediating an undetonated explosive charge abandoned in the ground.

Yet a further object of the present invention is to provide such apparatus, systems, and methods as are capable of remediating an undetonated explosive charge, even if the location of the explosive charge cannot be ascertained with any degree of certainty.

These and other objects and features of the present invention will become more fully apparent from the following description and appended claims, or will be appreciated by the practice of the invention.

To achieve the foregoing objects, and in accordance with the invention as embodied and broadly described herein, apparatus, systems, mixtures and methods are provided that remediate in situ an undetonated explosive utilizing the biological activity of microorganisms.

In one form, an apparatus incorporating teachings of the present invention includes a quantity of explosive material and microorganisms that are disposed in sufficient proximity to the quantity of the explosive material that the microorganisms can initiate bioremediation of the explosive material when the microorganisms are mobile. Similarly, an explosive mixture is formed by intermixing the microorganisms and the explosive material, which, when hydrated, activates the microorganisms to initiate bioremediation of the explosive material. The explosive apparatus preferably has a shell that enables water to flow through the shell to contact the explosive material. The shell may, for example, have an open end, have holes or be water permeable.

The apparatus or mixture may also further comprise a mobilization means for mobilizing the microorganism to contact the explosive material. The mobilization means enables the microorganisms to initiate bioremediation of the explosive material or to continue bioremediating the explosive material. The terms "mobile" and "mobility" refer to the ability of the microorganisms to move, to be activated or made "active," to be carried by the movement of a liquid, to be distributed to the explosive material or to be unrestricted in movement by a barrier that previously confined the microorganisms such that after the barrier is removed the microorganisms can contact the explosive material. The term "active" refers to the state of the microorganisms wherein the microorganisms can bioremediate explosives.

An example of a mobilization means that is useful with an explosive apparatus or an explosive mixture include a water-permeable container that enables water to contact the explosive material and microorganisms therein, and the addition of a porous material, such as foamed cellulose and/or starch, to the cast explosive to permit passage of moisture therethrough.

The microorganisms can be mobile or deactivated. Examples of deactivated microorganisms that typically require activation include microorganisms that have been dehydrated by air drying or through lyophilization. The microorganisms are preferably freeze dried to increase the survivability of the microorganisms during the forming process wherein the explosive material and microorganisms are combined. More specifically, it is desirable to heat the explosive material to increase the moldability of the explosive material and to enable the microorganisms and explosive material to be easily intermixed. However, the heat can be lethal to the microorganisms as the microorganisms are placed or mixed in the explosive material. Accordingly, the microorganisms have preferably been prepared such that the microorganisms can be characterized in that the microorganisms are sufficiently resistant to heat that a significant portion of the microorganisms survive the intermixing or placement process even when the process occurs at a temperature of about 100° C. Alternatively, the microorganisms can be incorporated within or on the surface of a foam material that acts as an insulator which protect microbes and nutrients from thermal damage.

The microorganisms can be disposed in close proximity to the explosive material or dispersed within the explosive material in many different forms. The microorganisms can be in various aggregations such as in chips, in or on foamed materials, and in or on porous materials. The aggregations can also be added without any processing of the microorganisms to form the microorganisms into a particular distinct form. Accordingly, the microorganisms can be present as a flake, granule, clump, powder or shard of a nutrient medium containing microorganisms. In a preferred embodiment, the microorganisms can be contained within one or more chips. More particularly, each chip can additionally include cellulose therein, the cellulose expanding upon contact with moisture to cause cracking of the chip and the cast explosive matrix, which contributes to the mobility of microorganisms.

Nutrients, in addition to the explosive material, are generally necessary for the microorganisms to survive and grow. A nutrient is any substance that provides nourishment to the microorganism, such as a mixture of trace nutrients or elements, and/or any substance providing a source of carbon, nitrogen, and phosphate. In a preferred embodiment of the invention, dispersal of casamino acids provides nourishment to the microorganisms and accelerates microorganism growth subsequent to a failed detonation. Binders are also often necessary and organic binders are preferred. Depending on the binder or nutrient utilized, one chemical can perform the function of both binder and nutrient. The thermal resistance of the microorganisms can also be increased by utilizing various thermal protection additives.

Ideally, the remediation occurs in two respects. The explosive is disabled from inadvertent detonation. Subsequently, the material composition of the explosive material is rendered relatively nonharmful.

In another embodiment of the invention, microorganisms are releasably contained by gelatin, a substance that is self-effacing when contacted by microorganisms under favorable conditions.

In yet another embodiment, microorganisms are applied directly to the exterior of the explosive material or to the shell of an explosive apparatus.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 1 is a cross-sectional elevation view of a first embodiment of an explosive apparatus comprising a pellet of microorganisms intermixed in the explosive material;

FIG. 2 is a partial cross-sectional elevation view of a second embodiment of an explosive apparatus which comprises an encapsulated pellet;

FIG. 3 is a partial cross-sectional elevation view of a third embodiment of an explosive apparatus which comprises an encapsulated suspension of microorganisms;

FIG. 4 is a partial cross-sectional elevation view of a fourth embodiment of an explosive apparatus which comprises shards of moist nutrient wafers containing microorganisms;

FIG. 5 is a partial cross-sectional elevation view of a fifth embodiment of an explosive apparatus comprising microorganism chips intermixed in the explosive material;

FIG. 6 is a partial cross-sectional elevation view of a sixth embodiment of an explosive apparatus comprising microorganism chips having cellulose therein intermixed in the explosive material;

FIG. 7 is a cross-sectional elevation view like that of FIG. 6 illustrating the explosive apparatus at a time subsequent to the expansion of cellulose and resulting cracking of the chips and the matrix of the cast explosive when water contacts the cellulose;

FIG. 8 is a partial cross-sectional elevation view of a seventh embodiment of an explosive apparatus comprising a carrier of foamed cellulose and/or starch, having a microorganism consortium therein or thereon, intermixed in the explosive material;

FIG. 9 is a partial cross-sectional elevation view of an eighth embodiment of the invention wherein the carrier of foamed cellulose and/or starch of FIG. 8 is disposed as a strip running the length of the explosive charge within the explosive matrix; and FIG. 10 is a partial cross-sectional elevation view of a ninth embodiment of the invention wherein the carrier of foamed cellulose and/or starch of FIG. 8 is disposed as a strip in the area surrounding the capwells of the explosive apparatus;

FIG. 11 is a partial cross-sectional elevation view of a tenth embodiment of an explosive apparatus which comprises a powder of microorganisms dispersed on top of the explosive material;

FIG. 12 is a partial cross-sectional elevation view of an eleventh embodiment of an explosive apparatus which depicts a chamber in the explosive material containing a suspension of microorganisms; and FIG. 13 is a partial cross-sectional elevation view of a twelfth embodiment of an explosive apparatus which comprises clumps of microorganisms within the shell of the apparatus.

DETAILED DESCRIPTION OF THE PREFERRED EMBODIMENTS

The present invention pertains to systems, apparatus, and methods for the in situ remediating of undetonated explosive charges. The methodology employs at least one type of microorganism that is capable of digesting an explosive material.

According to the teachings of the present invention, an explosive charge to be installed, for example by being buried in the ground, is so housed in a casing with the microorganisms. If the explosive charge fails to detonate, the explosive charge can then reliably be left undisturbed, and the microorganisms will digest or degrade the explosive material involved. Preferably, the explosive will be thereby both disabled from detonation and detoxified.

The terms "remediate" and "remediation" are used in the specification and the appended claims to refer generally to the conversion or transformation of an explosive material which is detonatable by shock or heat into a different chemical material which is less explosive or nonexplosive. The terms "bioremediate" and "bioremediation" are used to refer to remediation effected by the action of microorganisms. The present invention is thus one intended to bioremediate explosive materials.

The present invention has demonstrated an immediate utility relative to highly explosive materials, such as trinitrotoluene (TNT), pentaerythritol tetranitrate (PETN), cyclotrimethylene trinitramine (RDX), and cyclotetramethylene tetranitramine (HMX). These are typically utilized in seismic charges.

The term "bioremediable explosive" is used in the specification and the appended claims to refer to any explosive material which can be converted into a less explosive or nonexplosive material by the action of microorganisms, whether or not such microorganisms are explicitly disclosed herein. The highly explosive materials listed above are thus bioremediable explosives, since it has been demonstrated that at least the examples of microorganisms disclosed herein are capable of converting those high energy explosive materials into less explosive or nonexplosive materials.

Currently, on the basis exclusively of the examples of microorganisms disclosed herein, known bioremediative explosives include at least explosives which are classified as organic nitroaromatics, inorganic nitrates, organic nitramines, or organic nitric esters. Examples of organic nitroaromatics include TNT, hexanitrostilbene (HNS), hexanitroazobenzene (NAB), diaminotrinitrobenzene (DATB), and triaminotrinitrobenzene (TATB). Examples of organic nitramines include RDX, HMX, nitroguanidine (NQ), and 2,4,6-trinitrophenylmethylnitramine (tetryl). Examples of organic nitric esters include PETN, nitroglycerine, and ethylene glycol dinitrate. A suitable inorganic nitrate includes ammonium nitrate.

In one embodiment of the present invention, highly explosive materials, such as TNT and PETN, are converted through the action of microorganisms into less explosive materials. These intermediate chemicals can then be fully transformed into materials such as biomass and chemicals such as $CO_2$ and $N_2$. Optimally, the highly explosive materials are reduced according to the teachings of the present invention, first into less explosive intermediate chemicals or nonexplosive products. These intermediate chemicals can then be further transformed as needed into constituents which are either less explosive or less harmful as contaminants in the environment to the health of humans, animals or plants than the intermediate chemicals may be. The fmal product resulting from the metabolizing action of the microorganisms will thus include any number of combinations of elements that originated in the explosive material as constituted before the initiation of the bioremediation process.

The microorganisms comprise at least a first type of microorganism that disables or deactivates the explosive material by degrading the explosive material into less explosive materials or nonexplosive materials. The microorganisms may also further comprise a second type of microorganism that further bioremediates any intermediate chemicals resulting from the bioremediation action of the first type of microorganism to fully bioremediate the explosive material into nonexplosive materials.

Although any type of microorganism capable of converting explosive material into less harmful chemicals is considered to be within the scope of the present invention, examples of microorganisms that have been demonstrated to exhibit that capacity include the group consisting of Pseudomonas spp., Escherichia spp., Morganella spp., Rhodococcus spp., Comamonas spp., and denitrifying microorganisms. It is within the scope of the present invention to use any combination of these particular microorganisms, or of any other microorganisms that are determined to be capable of bioremediating explosive materials. Suitable Pseudomonas spp. microorganisms include microorganisms in the group consisting of aeruginosa, fluorescens, acidovorans, mendocina, cepacia, and an unidentified type.

The present invention thus utilizes any of numerous different selections of microorganisms capable of degrading explosive materials in any of various relative quantities. Each of these various selections of microorganisms will for convenience hereinafter and in the appended claims be referred to as a "microorganism consortium." In such a microorganism consortium, one type of microorganism can advantageously reduce the explosive material to a particular intermediate chemical, such as azoaromatics, while that type or another type of microorganism may then further reduce the azoaromatics or other intermediate chemicals to carbon chains, $CH_4$, $NH_3$, and $N_2$. In one presently preferred embodiment, such a microorganism consortium utilizes all or some of various of the microorganisms belonging to Pseudomonas spp., Escherichia spp., Morganella spp., Rhodococcus spp., Comamonas spp., and denitrifying microorganisms.

The bioremediation rate is an important variable in designing a system that is impacted by many factors. One factor that is closely related to the bioremediation rate of explosive materials by the microorganisms is the growth rate of the microorganisms. The growth rate of some species of microorganisms disclosed herein are logarithmic while others are only linear. Accordingly, the growth rate of the consortium depends on the type of microorganisms utilized. Additionally, the growth rate of the consortium of microorganisms depends on other factors, such as the availability of nutrients. The growth rate of the consortium of microorganisms can, however, be generally characterized as logarithmic.

A consortium of microorganisms within the scope of the present invention was deposited on May 23, 1996, with the American Type Culture Collection (hereinafter "ATCC") in accordance with the provisions of the Budapest Treaty on the International Recognition of the Deposit Microorganisms for the Purpose of Patent Procedure. The ATCC is located at 10801 University Boulevard, Manassas, Va. 20110-2209 U.S.A. The deposited consortium of microorganisms was assigned ATCC Designation No. 55784. For purposes of this disclosure, the microorganism consortium deposited with the ATCC and designated ATCC Designation No. 55784 is hereby incorporated by reference.

The microorganism consortium deposited with the ATCC was obtained from Richards Industrial Microbiology Laboratories, Inc. (hereinafter "RIML") located at 55 East Center, Pleasant Grove, Utah 84062 U.S.A. The microorganism consortium is identified at RIML by Product No. RL-247. Accordingly, microorganisms sold as RL-247 by RIML under the tradename RL-247 and assigned ATCC Designation No. 55784 are considered to be within the scope of the invention disclosed herein, whether or not constituent microorganisms therein are explicitly identified to any degree herein.

The microorganisms of the microorganism consortium are chosen for having a demonstrated ability to metabolize and degrade explosive materials in any way that contributes to the disabling of the explosive material or to the detoxification of the chemical components thereof. If microorganisms are selected that are both aerobic and anaerobic, bioremediation will occur in shallow and exposed surface locations, as well as in deep explosive boreholes. Ideally, the microorganisms selected for the microorganism consortium should be nonpathogenic and surfactant-producing, as this enhances the digestive action of the microorganism colony.

In one embodiment of a microorganism consortium chosen according to the teachings of the present invention, the Pseudomonas spp. are selected from the group consisting of aeruginosa, flourescens, acidovorans, mendocina, and cepacia. Any microorganisms of Pseudomonas spp. other than the microorganisms identified above are considered to be within the scope of the invention disclosed herein, provided that such microorganisms perform any of the functions described above having utility in the remediating of an explosive charge. Correspondingly, any microorganism is considered to be within the scope of the invention disclosed herein, provided the microorganism exhibits any utility relative to the bioremediating of explosive materials.

Thus, the disclosure and incorporation herein of the microorganism consortium assigned ATCC Designation No. 55784 or the disclosure of the microorganism consortium available from RIML under the tradename RL-247, are but examples of microorganism consortiums within the teachings of the present invention and are not limiting of the microorganisms that may be selected for inclusion in a microorganism consortium according to the teachings of the present invention.

Various embodiments of explosives are set forth hereinbelow which are configured to enable microorganisms to bioremediate a quantity of explosive material. The microorganisms are intermixed with or are disposed in sufficient proximity to the explosive material to allow the microorganisms to initiate bioremediation of the explosive material when the microorganisms are mobilized or activated (i.e., hydrated).

The shelf lives of the explosive material and the microorganisms are increased by delaying the bioremediation activity of the microorganisms at least until the explosive is ready to be utilized. Accordingly, the preferred embodiments involve the use of microorganisms that are temporarily immobilized or that have been inactivated until the explosive is to be positioned or has been positioned in the ground. Configurations can also be utilized wherein the microorganisms are initially mobile or active when positioned relative to the explosive material, thereby enabling the microorganisms to immediately initiate bioremediation.

The system of the current system forms a system for in situ bioremediating of an explosive material. The failure of installed explosives to detonate is primarily caused by the forces experienced during positioning of the system in the bottom of a borehole. The system is typically lowered into or driven down a borehole with a tamping pole. In the process, wires 26 are often broken or disconnected from detonators 24, so that detonation cannot occur. When this happens, the digestion of explosive material 30 by microorganisms (in the various illustrated forms depicted hereinafter, e.g., as pellets 32, capsules 40, shards 48, chips 60, or a foam material 66) will proceed in due course. Eventually, the explosive material 30 will be reduced to nonexplosive and non-harmful materials that are neither detonatable by any activities in the vicinity, nor are an environmental contaminant. Over time, by exposing an undetonated charge to the microorganisms, the entirety of the explosive material of the charge is reduced to a substance that cannot be detonated.

The time period required for the microorganisms to first disable an explosive, and then to fully remediate a given quantity of intermediate chemical materials, depends on the amount and type of explosive material used, as well as the composition of microorganism consortium used therewith. Depending on design, relative concentrations of the explosive, the time required can be days, weeks, months, or years.

FIGS. 1–13 depict embodiments of the present invention wherein microorganisms are intermixed in the explosive or are disposed against an exterior surface of the explosive material. The microorganisms depicted in FIGS. 1–13 are disposed in sufficient proximity to said quantity of explosive material that the microorganisms can initiate bioremediation of the explosive material when the microorganisms are mobile or activated.

Figure 2:
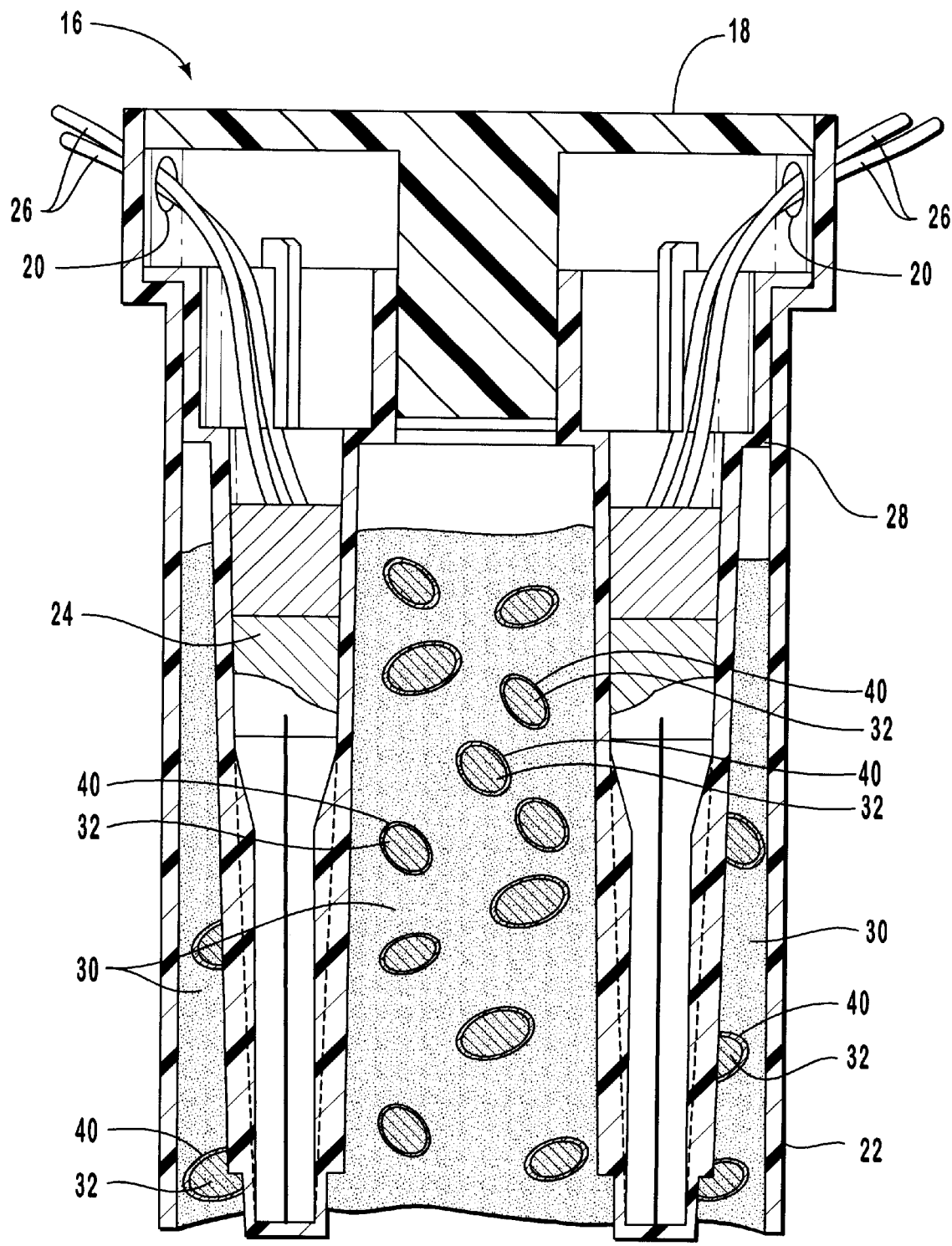
Figure 3:
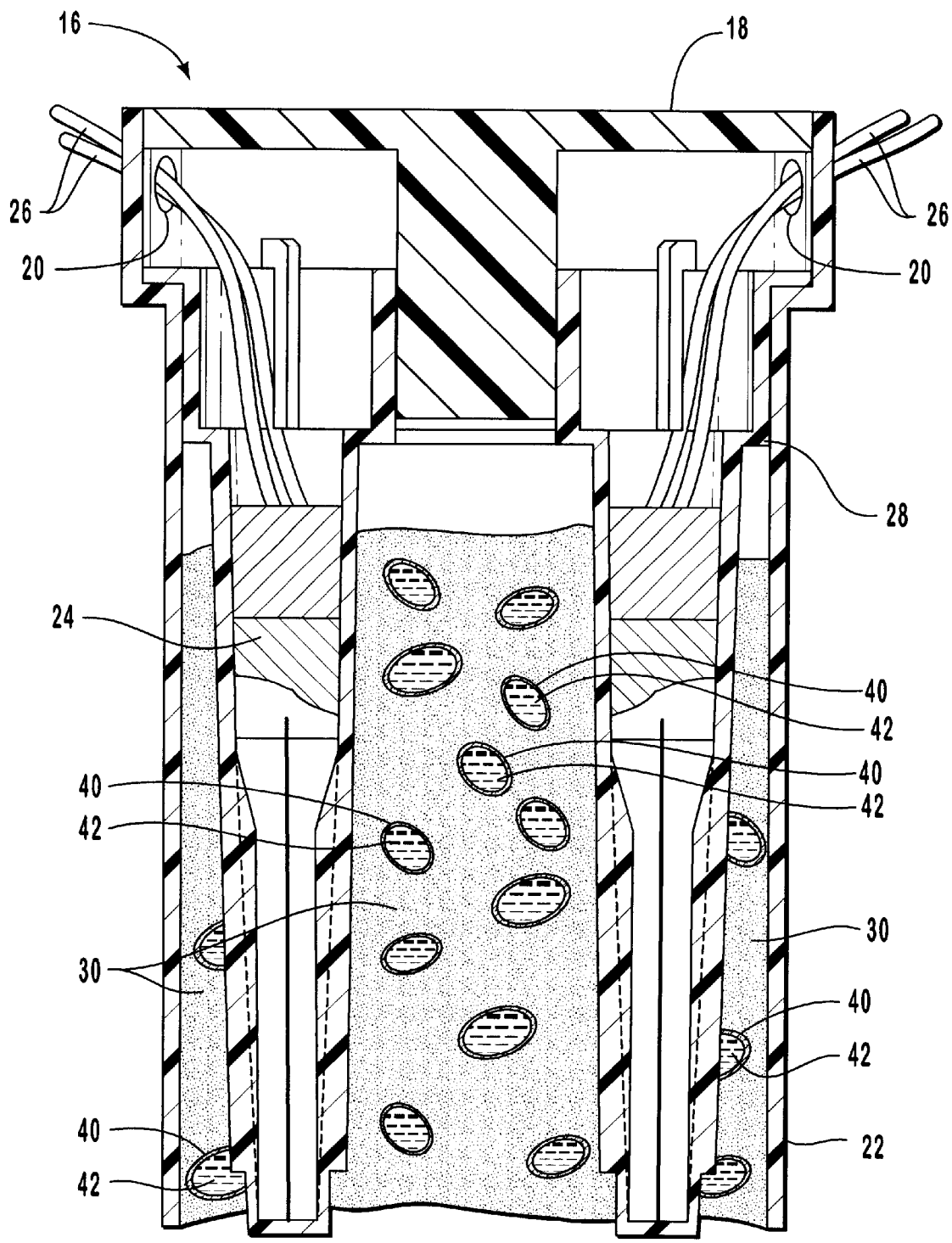
Figure 4:
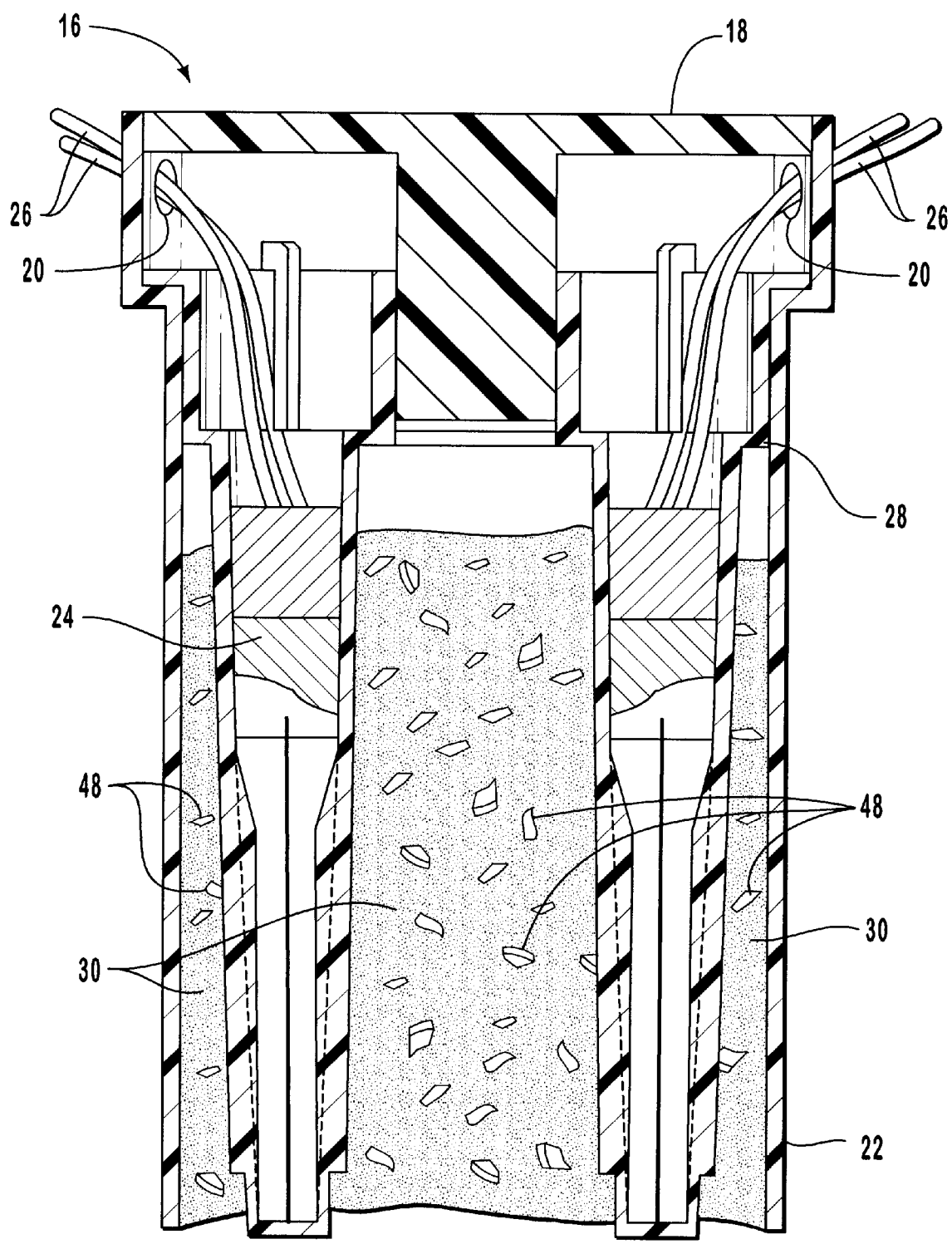
Figure 5:
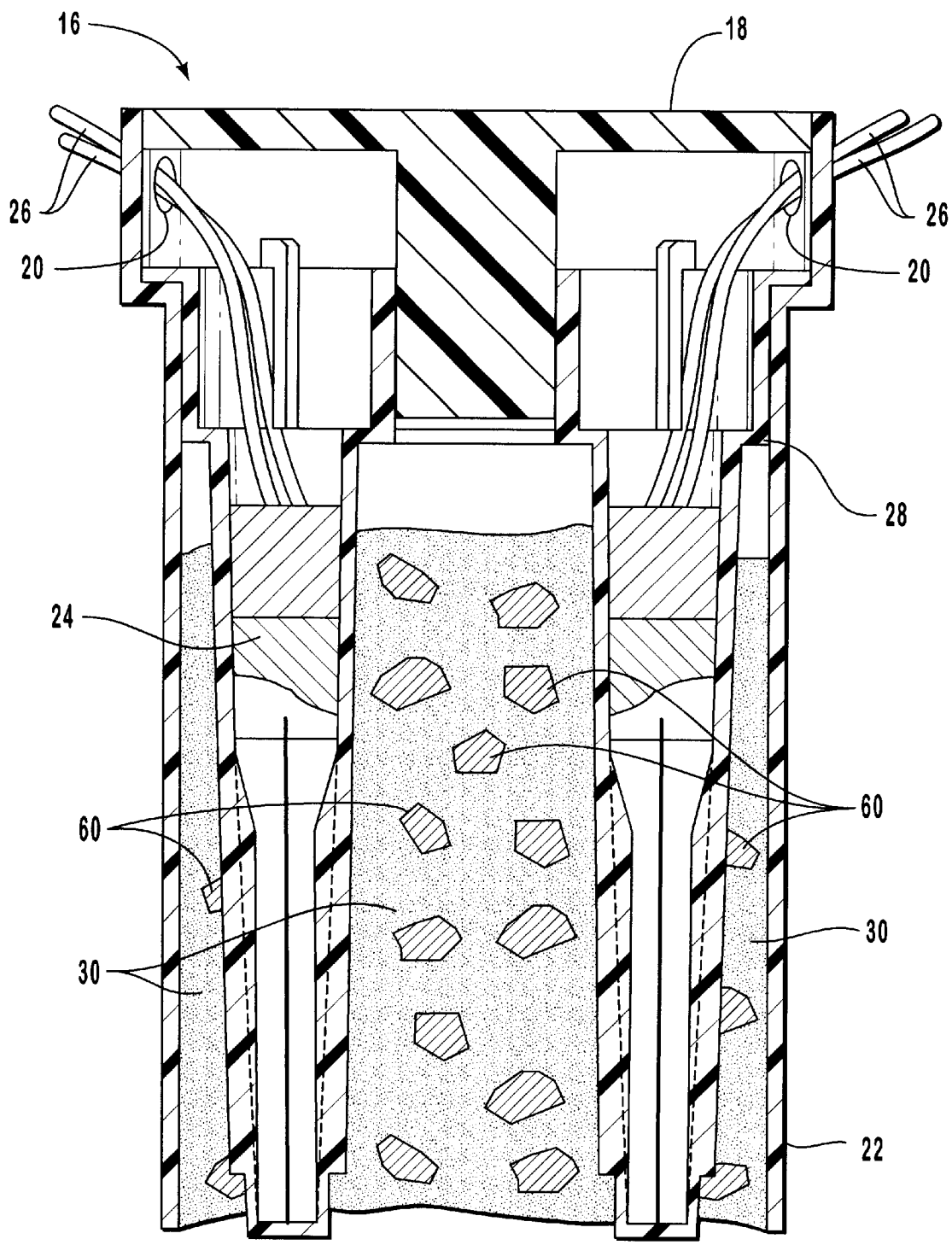
Figure 6:
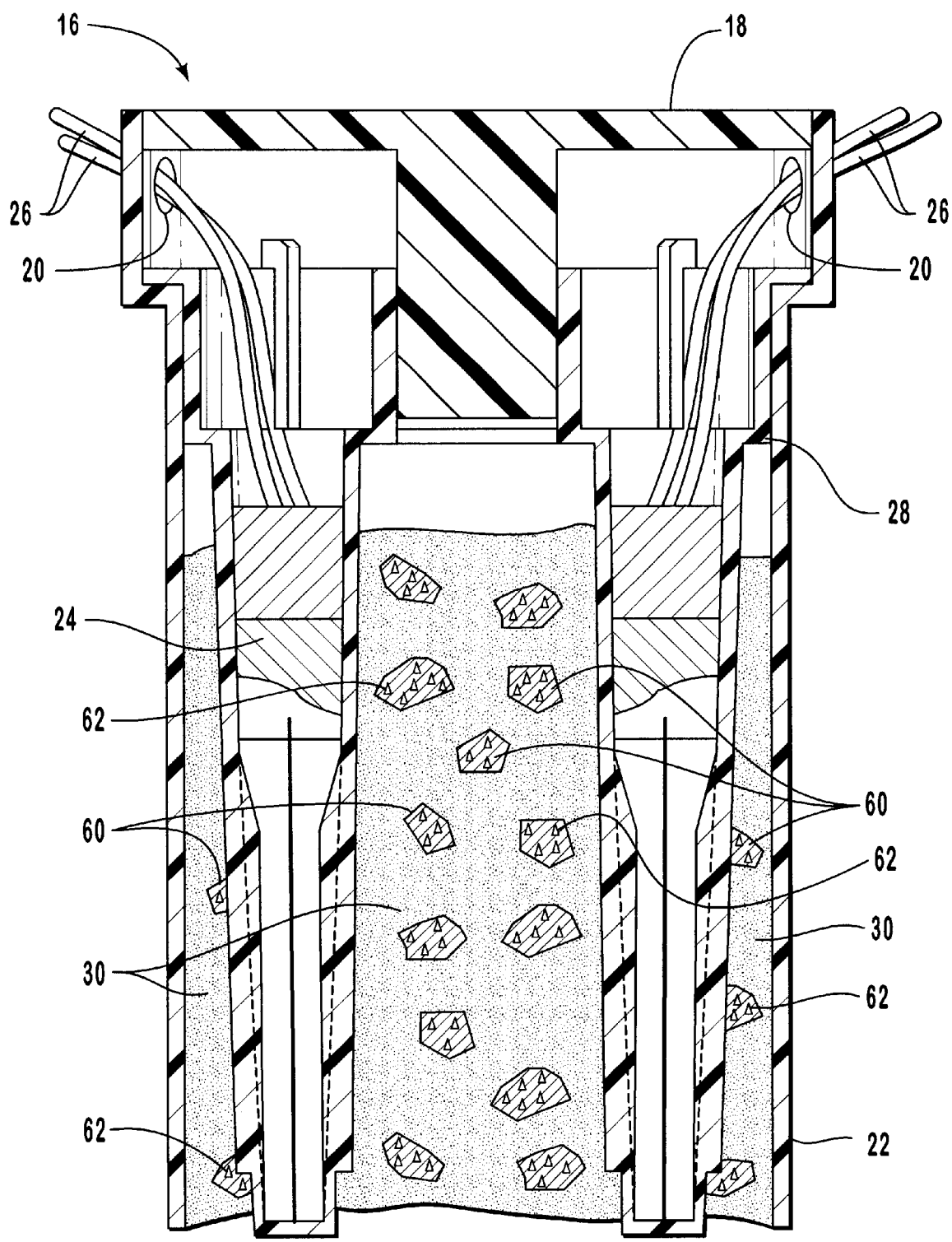
Figure 7:
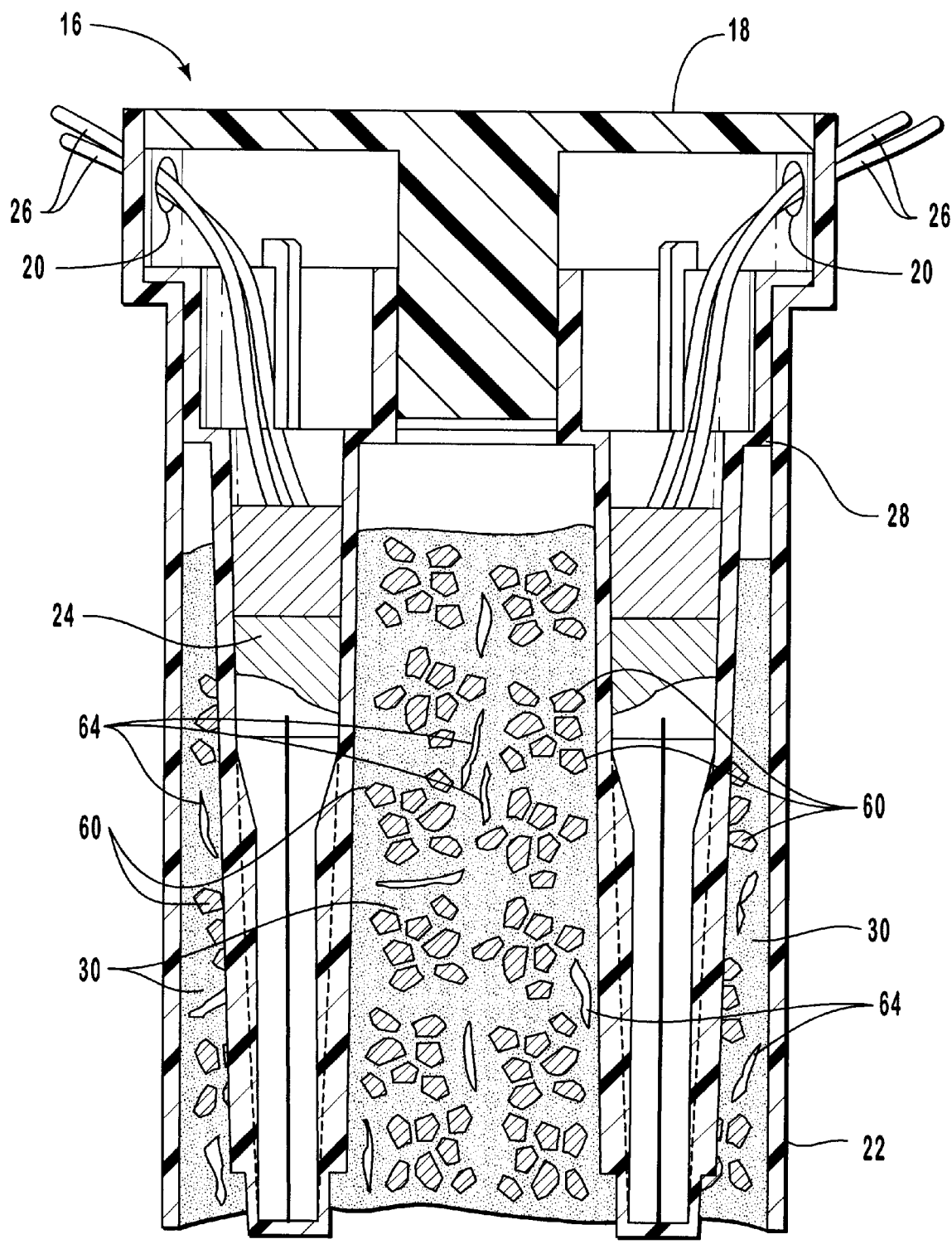
Figure 8:
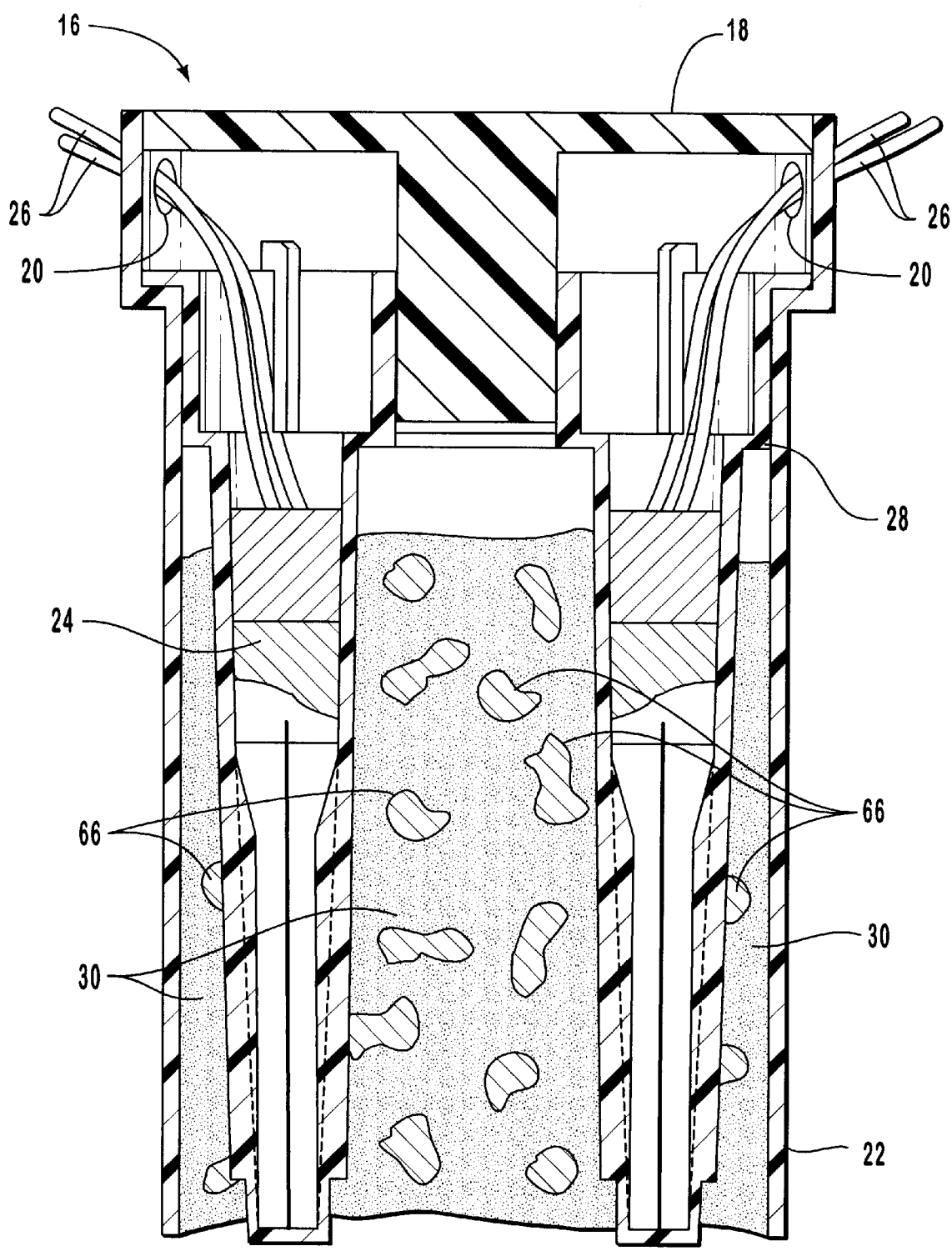
Figure 9:
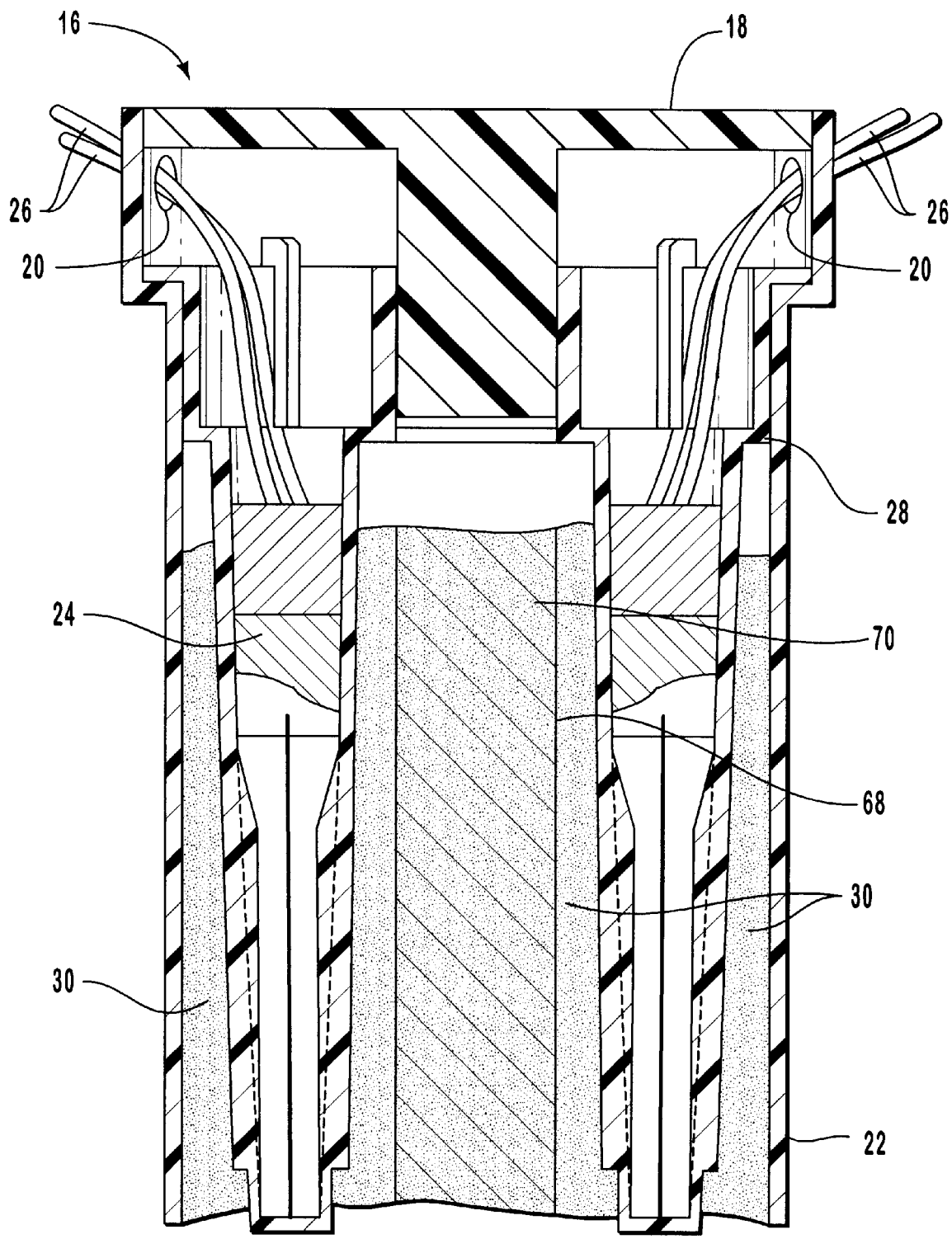
Figure 10:
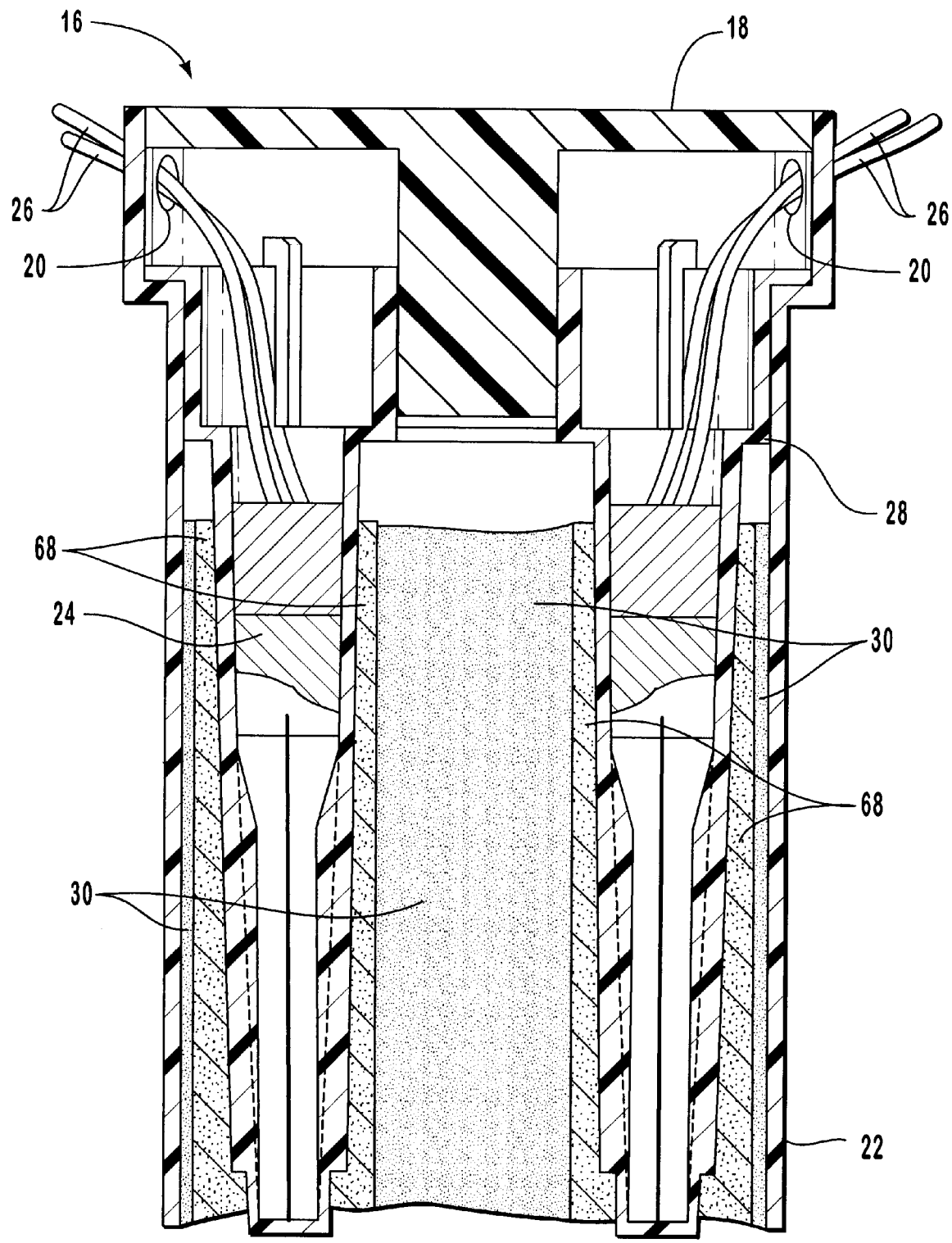
Figure 11:
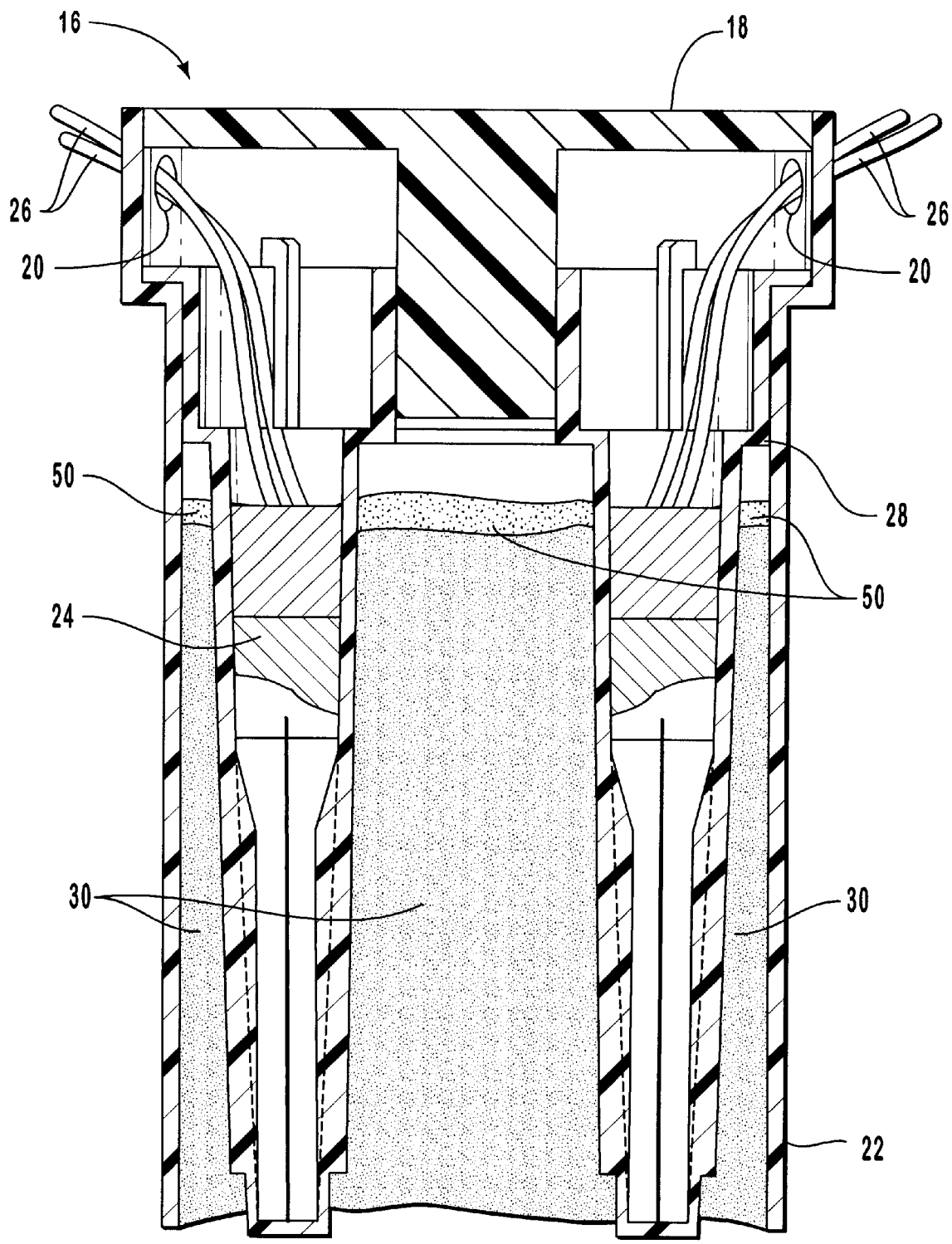
Figure 12:
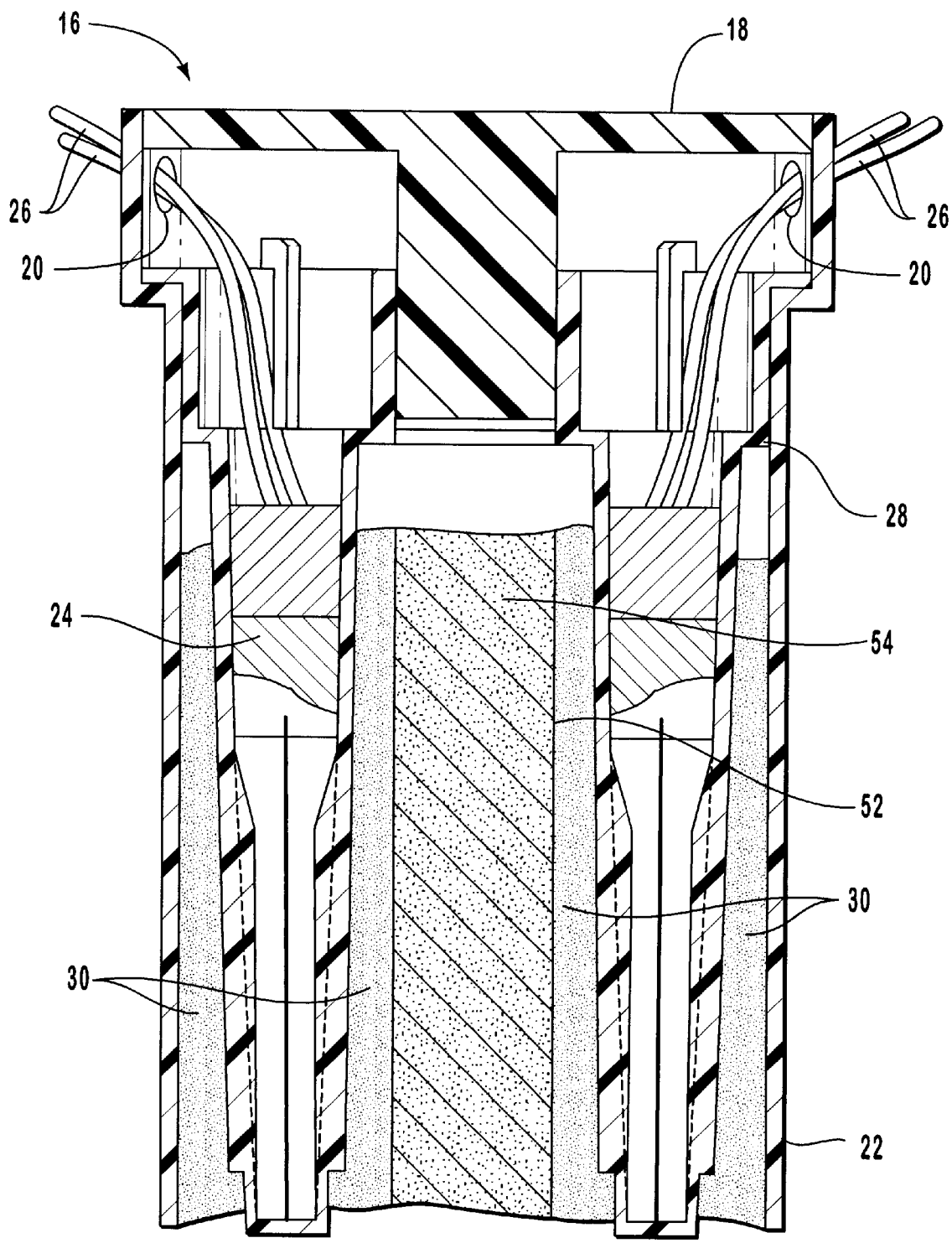
Figure 13:
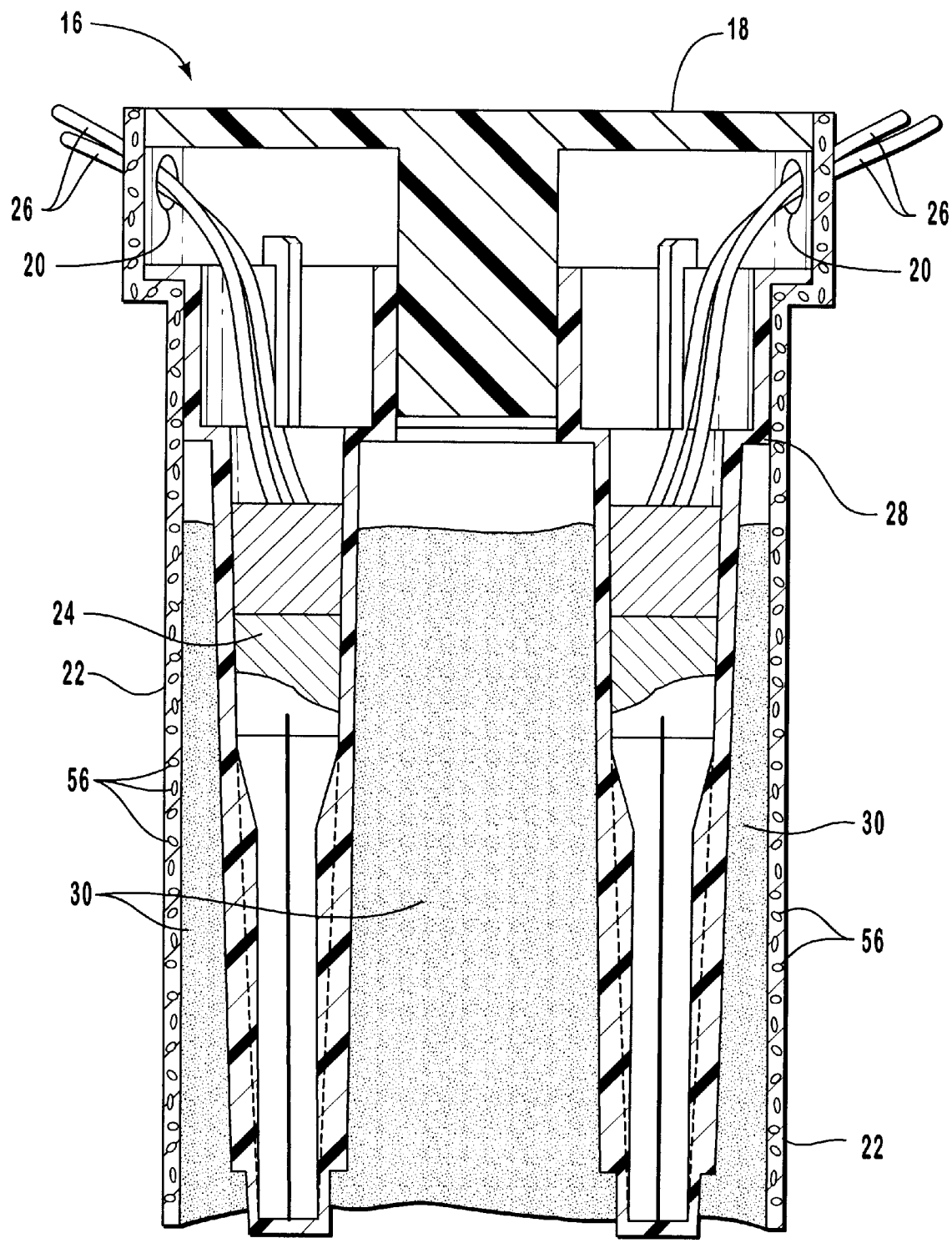

The microorganisms intermixed in the explosive material are generally in aggregations or clusters such as pellets as shown in FIG. 1, capsules as shown in FIGS. 2–3, or shards as shown in FIG. 4. The embodiments depicted in FIGS. 5–10 provide examples of microorganisms carried within or on the surface of various carriers, such as chips as shown in FIGS. 5–7, or a foam material as shown in FIGS. 8–10. The embodiments depicted in FIGS. 11–13 provide examples of microorganisms disposed against an exterior surface of the explosive material. FIG. 11 shows a powder of microorganisms dispersed on the top surface of the explosive material. FIG. 12 depicts microorganisms poured into a column within the explosive material. FIG. 13 depicts a cluster of microorganisms positioned within the shell that contains the microorganisms. In addition to the clusters, aggregations, or carriers disclosed in FIGS. 1–13, the microorganisms can be positioned in any form even as individual microorganisms.

FIG. 1 illustrates an explosive apparatus 16 configured with an optional cap 18 and access openings 20 for wires 26. Explosive apparatus 16 has a capwell 28 with detonators 24. Explosive apparatus 16 further comprises a shell 22 containing an explosive material 30 and pellets 32 of microorganisms dispersed throughout explosive material 30. Shell 22 preferably enables water to flow through shell 22 to contact the explosive material 30 or at least into contact with the microorganisms in pellets 32 at the exterior surfaces of explosive material 30. Shell 22 may for example have an open end wherein water can flow, have holes or be water permeable to enable water to enter into the pores of explosive material 30.

Pellets 32 are dispersed as needed. For example, pellets 32 can be randomly dispersed, as shown, or concentrated as needed to deactivate the explosive charge. Pellets 32 are preferably positioned to facilitate desensitization of the explosive apparatus by being concentrated within explosive material 30 around detonators 24.

Pellets 32 can be positioned within explosive material 30 by any method and in any desired concentration. Control of the concentration and dispersion of pellets 32 in the explosive material 30 is maximized by adding pellets 32 to explosive material 30 when explosive material 30 is in a liquid state. Explosive material 30 is in a liquid state when being formed into a desired configuration by pouring the explosive material into a mold or directly into shell 22. The forming temperature of the explosive material is around 100° C. which is generally lethal to the microorganisms. Accordingly, the exposure time of microorganisms in pellets 32 to lethal temperatures is preferably minimized by adding pellets 32 to explosive material 30 while explosive material 30 is being formed or cast into a desired shape. Pellets 32 can also be pressed into explosive material 30 when explosive material 30 is solid or semi-solid at the time that the charge is manufactured.

The microorganisms or pellets 32 containing the microorganisms are preferably heat resistant to increase the survivability of the microorganisms when added to explosive material 30. There are several methods, which can be utilized alone or in combination, for obtaining heat resistant microorganisms or pellets.

One method for obtaining heat resistant microorganisms involves lyophilizing the microorganisms before the microorganisms are added to the hot explosive material. The microorganisms can be dehydrated by allowing the water to evaporate or preferably by freeze drying the microorganisms. Freeze drying the microorganisms dramatically reduces the mortality of the microorganisms due to thermal stress from exposure to the molten explosive material during the pouring process. It is speculated that freeze dried microorganisms are less susceptible to the lethal temperature effects than a microorganisms in a moist environment because the water content in the moist microorganism provides better heat transfer to the vital and temperature sensitive internal structures. The water removed from the freeze dried microorganisms is replaced at a later time in sufficient quantity to activate and mobilize the microorganisms.

The survivability of the microorganisms to thermal stress is also increased by increasing the thickness of the pellets 32. Increasing the thickness of pellets 32 decreases the rate of heat transfer to the interior of pellets 32, thereby protecting the microorganisms in the interior to the extent that the residence time of the microorganisms in the hot melt is not excessive. When the exterior microorganisms are destroyed they act as a thermal insulator for the microorganisms within the interior. Suitable pellets generally have an average diameter of about 3 mm.

Another method for reducing the mortality of microorganisms due to thermal stress is achieved by adding the microorganisms and explosive material into a mold in thin layers. By adding the microorganisms and explosive material incrementally in thin layers the layers can quickly cool thereby minimizing the exposure time of the microorganisms to the hot melt.

The heat resistance can also be increased by slowly raising the growth temperature of the microorganisms. By slowly raising the temperature of the environment of the microorganisms over a period of time during their growth, the high temperature tolerance of the microorganisms is significantly increased. Microorganisms can be utilized which have been adaptively developed or which have also been genetically developed. The microorganisms are preferably developed to have a very high survivability rate even when exposed to temperatures as high as about 100° C. Even microorganisms which have not been adequately developed to survive exposure to temperatures as high as about 100° C. are very useful since the temperature decreases as it is transferred into the pellet, yielding a greater interior portion that survive compared to a pellet utilizing unconditioned microorganisms. Accordingly, all microorganisms that have been developed for high temperature tolerance are useful and yield a higher survivability rate.

Additionally, pellets 32 can also be formed from mixtures of microorganisms and thermal protection additives that increase the heat resistance of the microorganisms. Examples of additives which have been found to increase the survivability of microorganisms when thermally stressed include dry milk and bentonite clay. These viability enhancers also can be used as binders as they tend to bind the constituents in the pellet together and can also be a nutrient source for the microorganisms. Insulative aggregates with no binding capability or that are not nutrient sources can also be used to thermally protect the microorganisms.

The pellets can be formed by compressing the microorganisms together along with any other constituent materials such as nutrients, binders and insulative materials. As previously set forth, the same component can act as a nutrient, binder or an insulative material. Nutrients are generally necessary even when the microorganisms are lyophilized since they provide the microorganisms with all of the materials needed for the microorganisms to fully grow and multiply. The explosives generally provide carbon and nitrogen while the nutrients generally provide phosphate and other chemicals, including carbon and nitrogen. Any suitable nutrient can be utilized; however, depending on the type of nutrient utilized and the availability of the nutrient the growth rate can be influenced. In addition to the nutrients previously discussed such as starch, flour, bran, and milk; other suitable nutrients include milk sugar and minimal medium glycerol. A preferred nutrient includes a mixture of amino acids derived by the hydrolysis of casein, which are commonly referred to as "casamino acids." Many of these nutrients can also act as stabilizers, such as starch, flour, bran, milk, glycerol in addition to phosphate buffered saline.

It is not always necessary to add a component that acts only as a binder since many nutrients can be utilized as a binder which are then converted into nutrients when contacted by a sufficient quantity of water to solubilize the binder. In addition to the binders previously mentioned, any suitable binder can be utilized. The binder is preferably an inorganic binder. A product sold as Diatab is a particularly useful binder or tablet base. Other materials that can be utilized as a binder include acrylamide, alginic acid or alginate, ethylcellulose, guar gum and gelatin.

Pellets 32 can also be encapsulated in a capsule 40 as shown in FIG. 2. For purposes of simplicity, structures and elements shared in common between the device of FIG. 1 and the remaining embodiments of the present invention, discussed hereinafter, will be numbered identically. The microorganisms in capsule 40 can be freeze dried, then formed into a pellet and encapsulated or the capsule can be formed by encapsulating moist microorganisms or a suspension of microorganism by pouring the suspension into a capsule and then drying or freeze drying the capsule. Any suitable materials for forming capsule 40 can be utilized. Examples of suitable materials include gelatin, starch, alginate and acrylamide.

While it is preferred to form the explosive by placing pellets of dehydrated microorganisms into molten explosive material since the molten explosive material is easily and relatively quickly molded into a desired shape, it can decrease the viability of the microorganisms. Accordingly, it is also desirable to form pellets 32 from moist microorganisms. Depending on the amount of liquid present, it may be necessary to introduce the microorganisms into explosive material 30 as a suspension of microorganisms as shown at 42 in FIG. 3 that is contained in a capsule 40.

Microorganisms which are merely moist can also be encapsulated or can be introduced as shards 48 of a moist nutrient wafer containing microorganisms as shown in FIG. 4. Shards 48, which are fragments or flakes, can also be a nutrient wafer containing lyophilized microorganisms.

The microorganisms intermixed in the explosive material can also be incorporated on any surface of or within a carrier material disposed within the explosive material. The term "carrier" is used generally in the specification to refer to a medium or material, including any surface thereof, within which microorganisms can be deposited or upon which microorganisms can be disposed. The carrier can be formed of any suitable material and can be shaped in a variety of patterns, as further depicted hereinafter, by way of example, in FIGS. 5–10.

As previously described in conjunction with the embodiment of FIG. 1, the carrier containing the microorganism can be randomly dispersed or concentrated as needed to deactivate the explosive charge. Likewise, the carrier can be positioned within explosive material 30 by any method and in any desired concentration. Heat resistance of the microorganisms can be accomplished or improved through a variety of techniques. For example, heat resistant microorganisms can be obtained by lyophilizing, dehydrating, or freeze drying the microorganisms prior to addition of the same to the hot explosive material. The survivability of the microorganisms to thermal stress can also be raised by increasing the thickness of the carrier, by forming the carrier of heat-resistant or insulative materials, and by including thermally-protective or insulative additives to the carrier. The carrier can also include other constituent materials such as nutrients, binders, and explosive materials. Formation of the explosive can be accomplished according to the various methods previously described in conjunction with FIG. 1.

FIG. 5 illustrates an explosive apparatus 16 including a carrier in the form of chips 60 containing microorganisms. Chips 60 are dispersed, as needed, within the explosive material 30 to deactivate the explosive charge. For example, the chips 60 can be randomly dispersed throughout the explosive material 30 matrix, as shown. Alternatively, the chips 60 can be selectively concentrated within the explosive material 30 around the detonators 24 to facilitate desensitization of the explosive apparatus at the initial point of discharge.

Various of the previously-described nutrients can also be intermixed with the explosive material 30 for the purpose of supplementally nourishing the microorganisms and accelerating initial microorganism growth subsequent to a failed detonation. The nutrients are preferably dispersed throughout the matrix of the explosive material 30 prior to casting the molten explosive about the chips 60 containing the microorganisms. The addition of nutrients to the explosive material 30 creates a fertile environment for microorganism growth upon activation or mobilization of the microorganisms.

A nutrient is any substance that provides nourishment to the microorganisms, such as a mixture of trace nutrients or elements, and/or any substance providing a source of carbon, nitrogen, and phosphate. A preferred nutrient includes a mixture of casamino acids. It has been discovered that the addition of the casamino acids mixture to the explosive material 30 significantly improves the performance of the microorganisms both in terms of the rate of explosive degradation and in terms of the completeness of the degradation process.

The chips 60 can additionally include cellulose 62, as shown in FIG. 6. The cellulose 62 contained within the chips 60 swells in size when contacted by water. This swelling of the cellulose 62 mechanically expands the chips 60 and promotes cracking (illustrated as cracks 64) in the matrix of the cast explosive material 30 when the chips 60 are contacted by moisture, as illustrated in FIG. 7. The cracking of the chips 30 and the matrix of the explosive material 30 aides mobilization and travel of the microorganisms throughout the shell 22 containing the explosive charge. Cellulose 62 can be incorporated into the chips 60 by any suitable means and in any suitable form, such as by forming a homogenous mixture of cellulose 62 within the chips 60 or by incorporating cellulose 62 particles within the chips 60, as shown in FIG. 6.

FIGS. 8–10 depict several embodiments of the invention wherein the carrier is formed of a foam material. Suitable foam materials for use in the present embodiment include any material having a lightweight cellular form resulting from introduction of gas bubbles during manufacture. Preferably, the foam material used in the instant embodiment is any commercially-available foam material used for packaging applications that is made of starch and cellulose. The foam material may be formed into any suitable and conceivable shape, such as the "peanut" shape 66 shown in FIG. 8, or a strip 68 placed along the length of the explosive apparatus 16, as shown in FIG. 9, or in proximity to the capwells 28 of the explosive apparatus 16, as shown in FIG. 10.

The microorganisms can be incorporated into the foam material or onto the surface of the foam material. The microorganisms being added to the foam material can be in any suitable state, such as a lyophilized or active state. As previously described with reference to other embodiments, nutrient can be also added to the foam material. Additionally, the foam material can be compounded to include explosive materials therein.

The use of a foam material provides a number of advantages. Due to the inherent insulative properties of foam materials, the use of foam as a carrier provides protection of microorganisms and nutrients from thermal damage. The use of foam materials specifically reduce the mortality of microorganisms and decomposition of the nutrients when the microorganisms and nutrients are added to high-temperature explosive materials during the aforementioned formation process.

Use of the foam material also provides advantages in the production process, such as the ability to add nutrient and microorganisms simultaneously prior to incorporation of the foam material into or proximate the explosive material 30. Through the use of a foam material, the quantity of microorganisms and/or nutrient can be more accurately controlled.

The foam material, being an absorbent material, facilitates transport of water throughout the explosive material 30 by acting as a water wick. The water absorption rate of the foam material can be controlled by modification of the density or composition of the foam material. Thus, the foam material can be used to transport microorganisms and/or nutrients contained therein to specific areas or throughout the explosive material 30, depending on the placement of the foam material.

The use of a foam material facilitates the highly accurate placement of the microorganisms and/or nutrient in the explosive charge. Such accurate placement can enhance activity of the microorganisms. For example, the foam material can be in the form of peanuts or beads 66 intermixed within the explosive material 30, as shown in FIG. 8. Due to the absorbent nature of foam materials, this configuration enhances mobility and activation of the microorganisms and/or nutrients, and further facilitates transport of water throughout the explosive material 30 matrix to promote the bioremediation process.

Alternatively, the foam material can be formed as strip 68 and be positioned to run the length of the charge through the explosive material 30 matrix, as shown in FIG. 9. As previously suggested, the foam strip 68 can include, in addition to microorganisms and/or nutrients, an explosive material 70. The explosive material 70 can be the same or different than the explosive material 30 used as the primary explosive charge. Because the foam strip 68 is not surrounded by the explosive material 30 on all surfaces, the foam strip 68 can be directly contacted by water. Thus, this particular embodiment advantageously does not rely primarily on the porosity of explosive material 30 for mobilization of the microorganisms.

As more fully detailed hereinafter, means for mobilizing the microorganisms to contact explosive material 30 is dependent on the ability of the microorganisms to be contacted by water, which in turn, depends on the porosity of the explosive material 30. Thus, the improved water contact afforded in the present embodiment enables the microorganisms to move within explosive material 30 and continue bioremediating the explosive material 30. The improved porosity also enables water to enter into the pores and come into contact with inactivate microorganisms and activate the microorganisms.

The foam strip 68 can also be positioned as strips 68 surrounding the capwells 28 of the explosive apparatus 16, as shown in FIG. 10. This particular placement of the foam strip 68 permits the digestive activity of microorganisms to disarm explosive material 30 by first attacking the area around the capwell 28 end of the explosive apparatus. This is where detonation is actually initiated. There is, however, no overall detrimental effect on the ability of an explosive charge to be detonated immediately after being initially contacted by bioremediating microorganisms. The initial activity of the microorganisms in the vicinity of the capwell can advantageously prevent accidental detonation of the explosive charge which can be caused, for example, by digging in the area of the explosive charge after the explosive charge is positioned in a borehole.

Additionally, when the foam strip 68 is contacted by sufficient quantities of water, the water saturates and/or dissolves the foam to displace the explosive contained therein or in the surrounding areas. This is of particular value if the foam strip 68 is formed around the capwell 28, resulting in rapid disarming of the charge.

Clusters or aggregations of moist microorganisms in configurations such as pellets, capsules, shards, flakes, chips, foam materials and the like are preferably blended into explosive material 30 and then pressed into a mold. Moist microorganism clusters can also be pressed into explosive material 30. When the microorganisms are in a moist state but are blocked from contact with the explosive material or are not sufficiently mobile, nutrients provide a minimal food source until the microorganisms can metabolize the explosive material. After the mixture is shaped into an explosive charge and the microorganisms are sufficiently moist it will bioremediate automatically within a predetermined time following manufacture.

An explosive apparatus is often left underground for periods of time up to six months and even up to a year. Accordingly, an explosive apparatus is preferably explodable for up to about six months and more preferably for up to about a year.

As previously set forth, the microorganisms can be concentrated around detonators 24 to desensitize the explosive since detonators 24 are typically more sensitive to impact and friction than explosive material 30. The time required to desensitize explosive apparatus 16 by disabling explosive material 30 around detonators 24 is dependent on many variables in addition to the distribution of the microorganisms, the growth rate of the types of microorganisms utilized, the ratio of microorganisms to explosives, the availability of particular nutrients, the types of microorganisms and explosives utilized and other physical condition such as pH, water availability and temperature. These same variables generally determine the time required to reduce explosive material 30 to a residual or negligible amount and the time required to entirely reduce explosive material 30 to a nonhazardous and preferably nonharmful material. Some of these additional variables include the amount of surface area exposed to the microorganisms, the mobility of the microorganisms, and the porosity of the explosive materials. Accordingly, the bioremediation rate can be designed as needed.

The porosity of the explosive materials is an example of a mobilization means for mobilizing the microorganisms to contact explosive material 30. The porosity of the explosive material 30 enables the mobilized microorganisms to move within explosive material 30 and continue bioremediating explosive material 30. The porosity also enables water to enter into the pores and come into contact with the microorganisms and mobilize the microorganisms. A surfactant in explosive material 30 is another example of a mobilization means. Surfactants facilitate wetting of the crystals in explosive material 30 which enhances the mobility of the microorganisms and the accessibility of the crystals to the microorganisms.

Explosive apparatus 16 can be immersed in water before being placed in a borehole to allow water to pass through shell 22 and enter into the pores to mobilize the microorganisms or clusters thereof intermixed in explosive material 30. Explosive apparatus 16 can also be exposed to a vacuum before being dipped in water. It is generally not necessary to immerse explosive apparatus 16 in water as groundwater is almost always present in the borehole. Water can also be poured into the borehole as needed. Water around or in contact with explosive apparatus 16 are representative examples of mobilization means for mobilizing the microorganisms. Additionally, the explosive apparatus 16 can be coupled to a reservoir means or apparatus which releasably contains a liquid, such as water, for mixing into or around the explosive apparatus 16.

Since groundwater is almost always in a borehole, it is generally desirable to design the explosive apparatus to utilize the groundwater. Accordingly, the porosity is preferably conducive to optimal capillary action through a network of microchannels. The network of microchannels or pores is sufficiently interconnected to provide optimal accessibility to the microorganisms by water and to provide optimal mobility to the mobilized microorganisms. The porosity is also designed to provide optimal surface area for the microorganisms to bioremediate. The porosity is balanced against the amount of explosive material that is preferably present and any necessary amount of mechanical strength for withstanding crushing and other forces experienced while being positioned in the borehole. The porosity can also be heterogenous throughout explosive material 30 such that the area around detonators 24 is more porous compared to other sections to expose more surface area.

The embodiments depicted in FIG. 1–8 are dependent primarily on the porosity of explosive material 30 to provide access to the microorganisms and to provide mobilization pathways for the mobilized microorganisms. FIGS. 9 and 10, described above, and FIGS. 11–13 depict embodiments of the present invention that do not rely primarily on the porosity of explosive material 30.

FIG. 11 depicts microorganisms deposited as granules 50 on top of explosive material 30. Accordingly, as water passes through shell 22 the initial bioremediation activity of all of the microorganisms is concentrated at the portion of explosive material around detonators 24.

FIG. 12 depicts a chamber 52 centrally and longitudinally located within explosive material 30 that contains a suspension 54 of microorganisms. Microorganisms can also be positioned in chamber 52 which are merely moist or have been lyophilized. This configuration enables the mobilized microorganisms to bioremediate explosive material 30 from within a particular location in explosive material. The position of chamber 52 provides for controlled bioremediation of explosive material 30 around detonators 24.

FIG. 13 depicts another embodiment wherein shell 22 contains clumps 56 of microorganisms. Shell 22 is preferably formed from a material that is not only water permeable but also sufficiently water soluble to release the microorganisms contained in the shell. Examples of suitable materials include but are not limited to paper and polyvinyl alcohol. The microorganisms can then bioremediate explosive material 30 by beginning at the exterior of explosive material 30.

Yet another method of bioremediating explosives involves installing an explosive charge in a detonation site, such as a borehole, and then positioning microorganisms around the explosive charge by depositing microorganisms directly on the explosive charge and the detonation site. Similarly, a solution of microorganisms can be deposited at a detonation site. Then the explosive charge is placed in the suspension of microorganisms. Additionally, an explosive apparatus can be sprayed with or soaked in a suspension of microorganisms before being installed at a given detonation site, preferably while being exposed to a vacuum.

Experiments were conducted to study the process of remediating explosive materials according to the teachings of the present invention. To do so, a microorganism consortium was derived from soil and water samples obtained on the property of an established explosive manufacturer located at 8305 South Highway 6, Spanish Fork, Utah 84660 U.S.A. The microorganism consortium in the form of a suspension was combined with various types of explosive materials, either in solid form or in an aqueous suspension, and the results were observed and documented. The results of several of these tests are set forth below as examples.

EXAMPLE 1

Quantities of the explosive materials TNT and PETN in water were combined with the suspension of the microorganism consortium. The resulting mixture initially included 47.23 ppm of PETN and 40.63 PPM of TNT. The mixture was divided among containers that were stored in aerobic conditions at ambient temperature for various time periods. Table 1 below indicates the explosive analysis of these samples after each designated time interval. The explosive materials were substantially degraded after a period of five weeks.

TABLE 1

Aerobic Bioremediation of TNT and PETN

| Explosive Material | Initial Analysis | Analysis After 3 Days | Analysis After 5 Weeks |
|---|---|---|---|
| PETN | 47.23 ppm | 40.94 ppm | 7.25 ppm |
| TNT | 40.63 ppm | 5.32 ppm | 0.62 ppm |

EXAMPLE 2

The mixture prepared in Example 1 was stored in anaerobic conditions at ambient temperature and observed. The results were determined by HPLC analysis in ppm and averaged. Table 2 below sets forth the results obtained. As can be seen by comparing the results in Table 2 with the results in Table 1, the explosive materials tested remediated more rapidly under anaerobic conditions than under aerobic conditions.

TABLE 2

Anaerobic Bioremediation of PETN and TNT

| Explosive Material | Initial Analysis | Analysis after 3 Days | Analysis after 1 Week | Analysis after 5 Weeks |
|---|---|---|---|---|
| PETN | 47.23 ppm | 28.31 ppm | 24.46 ppm | 0.82 ppm |
| TNT | 40.63 ppm | 0.31 ppm avg. | 0.31 ppm avg. | None |

EXAMPLE 3

Discs of the explosive material Pentolite having a diameter of a pencil were split in two. When the discs were split each weighed about 0.1 gram. The discs were placed either in water as a control or in 6 ml to 8 ml of a suspension of the microorganism consortium. After a specific amount of time in aerobic conditions, the discs were dried and weighed or analyzed by HPLC. The liquid portions were analyzed by HPLC. The net remediated weight loss in the explosive material was determined by subtracting the control weight loss as a percentage from the weight loss as a percentage in each remediated explosive. The explosive loss by degradation is listed in Table 3 for each of the samples. The samples in B and C were tested for longer periods of time than the sample in A. The results of the testing of samples B and C show that significant bioremediation did not occur beyond the level achieved in sample A. This was most likely due to insufficient quantities of nutrients in samples B and C as the bioremediation activity probably ceased when the nutrients were consumed.

TABLE 3

Aerobic Bioremediation of Pentolite

| Sample No. | Sample or Test | Time | Initial Weight | Final dry weight plus weight of explosive in liquid portion. | Net Remediated Weight Loss |
|---|---|---|---|---|---|
| A | Control | 22 days | 0.1355 g | 0.1266 g = 6.57% loss | 6.97% Net Loss |
|   | Test | 22 days | 0.0981 g | 0.0848 g = 13.54% loss | |
| B | Control | 88 days | 0.0578 g | 0.0557 g = 3.63% loss | 5.52% Net Explosive Loss |
|   | Test | 88 days | 0.0743 g | 0.0675 g = 9.15% loss | |
| C | Control | 173 days | 0.1236 g | 0.1236 g = no loss | 6.78% Net Explosive Loss |
|   | Test | 173 days | 0.0737 g | 0.0687 g = 6.78% loss | |

EXAMPLE 4

Experiments were conducted to compare remediation rates under aerobic and anaerobic conditions. Separate 5 gram samples of PETN/TNT Pentolite in a ratio of 60:40 were analyzed and placed in 100 ml to 300 ml suspension of a microorganism consortium. One was subjected to aerobic conditions; the other was subjected to anaerobic conditions. After various periods of time the samples were removed, air dried, and weighed to determine the amount of explosive material that had not degraded. The weight of the remaining explosive material was subtracted from the original weight to determine the weight of the explosive material lost due to bioremediation. The results are listed in Table 4 below. The results indicate that an insufficient amount of microorganisms were utilized or that the amount of nutrient was insufficient particularly in light of the results obtained in the other examples.

TABLE 4

Aerobic and Anaerobic Bioremediation of Pentolite

| Condition: Aerobic or Anaerobic | Original Weight | Time | Percent Wt Loss at Time listed | Time | Percent Wt Loss at Time Listed |
|---|---|---|---|---|---|
| Aerobic | 5.015 g | 66 days | 3.21% | 163 days | 5.43% |
| Anaerobic | 6.9027 g | — | — | 179 days | 3.10% |

EXAMPLE 5

Also investigated was the remediation according to the present invention of low levels of explosive materials in water. The explosive materials RDX and PETN were mixed with the water, combined with a suspension of a microorganism consortium, and then stored. The samples were tested by HPLC for explosive content initially and after 2 weeks. As shown in Table 5 below the bioremediation was nearly complete after two weeks.

TABLE 5

Bioremediation of Suspension of RDX and PETN

| Explosive Material | Initial Analysis | Analysis after 2 weeks |
|---|---|---|
| RDX | 6.6 ppm | Not detected |
| PETN | 25.0 ppm | Less than 0.5 ppm |

EXAMPLE 6

The remediation according to the present invention of soil contaminated with an explosive material was also investigated. Soil contaminated with the explosive material PETN was mixed with a suspension of a microorganism consortium and stored at ambient temperature. Samples were analyzed initially, after 44 days, and finally after 125 days. The PETN content in the soil dropped from 1659 ppm to 551 ppm. The results are set forth in Table 6 below.

TABLE 6

Bioremediation of Soil Contaminated with PETN

| Initial Analysis | Analysis after 44 Days | Analysis after 125 Days |
|---|---|---|
| 1659.2 ppm | 1193.2 ppm | 551.8 ppm |

EXAMPLE 7

In order to determine the effect of temperature on the growth of microorganism samples, the natural high temperature tolerances of the microorganism consortium were evaluated. The microorganism cultures were adapted to higher temperatures by slowly raising the growth temperature. By raising the temperature, the upper and lower limits of growth were both shifted upwards.

Two separate microbial growth stages were evaluated: the log phase, wherein the microorganisms experience logarithmic growth, and the stationary phase, wherein the microorganisms reach maximum growth. Microorganism cultures that enter the stationary phase late in their growth cycle induce the expression of genes which protect the microorganisms from various environmental stresses.

Four separate microorganism cultures were established. One culture, referred to as "30° C./Log Phase Culture", was comprised of new inocula, experiencing logarithmic growth, in fresh minimal medium, with TNT extract as the sole nitrogen source, and grown at 30° C. for three days. A second culture, referred to as "30° C./Stationary Phase Culture", was comprised of microorganisms that had reached maximum growth, in minimal mediur, with TNT extract as the sole nitrogen source, previously grown at room temperature for several weeks, and additionally grown at 30° C. for three days. The third culture, referred to as "37° C./Log Phase Culture", was comprised of new inocula, experiencing logarithmic growth, in fresh minimal medium, with TNT extract as the sole nitrogen source, and grown at 37° C. for three days. The final culture, referred to as "37° C./Stationary Phase Culture", was comprised of microorganisms that had reached maximum growth, in minimal medium, with TNT extract as the sole nitrogen source, previously grown at room temperature for several weeks, and additionally grown at 37° C. for three days.

Samples of the four different microorganism cultures were subjected to temperatures ranging from 30° C. to 97° C. for twenty minutes. A small sample of each heated culture and a non-heated control culture were spread-plated on both nutrient agar plates, and minimal medium with 10% glycerol plates. The plates were incubated overnight at 30° C.

The microbial growth was evaluated according to the number of colony forming units of the plate or the visualization of distinct colonies. The results of this evaluation are illustrated in Table 7, below. Microbial growth covering the entire plate with few, if any, single colonies, was referred to as "total". Microbial growth greater than 1000 clearly defined colonies per plate, or too numerous to count, was referred to as ">1000". If the density of the sample was only slightly less than the density of the previous sample, an asterisk "*" appears after the notation. At the lower density levels, the colonies were distinguishable as comprising at least bacteria, "B" or fungus/filamentous bacteria, "F". The number preceding "B" or "F" corresponds to the number of distinct colonies.

TABLE 7

Temperature tolerance of microorganism consortium.

| Temp. ° C. | 30° C./Log Phase Culture | 30° C./ Stationary Phase Culture | 37° C./ Log Phase Culture | 37° C./ Stationary Phase Culture |
|---|---|---|---|---|
| Control | Total | >1000 | Total | >1000 |
| 30° C. | Total | >1000 | Total | >1000 |
| 37° C. | Total | >1000 | Total | >1000 |
| 42° C. | Total | >1000* | Total | >1000 |
| 47° C. | Total* | >1000* | Total* | >1000 |
| 52° C. | 130 B | 180 F | Total* | 7 F |
| 57° C. | 0 colonies | 0 colonies | 0 colonies | 0 colonies |
| 62° C. | 0 colonies | 0 colonies | 0 colonies | 0 colonies |
| 67° C. | 0 colonies | 0 colonies | 2 colonies | 0 colonies |
| Control | Total | >1000 | Total | >1000 |
| 72° C. | 0 colonies | 0 colonies | 0 colonies | 0 colonies |
| 77° C. | 0 colonies | 0 colonies | 0 colonies | 0 colonies |
| 82° C. | 2 colonies | 0 colonies | 1 colony | 0 colonies |

TABLE 7-continued

Temperature tolerance of microorganism consortium.

| Temp. °C. | 30° C./Log Phase Culture | 30° C./ Stationary Phase Culture | 37° C./ Log Phase Culture | 37° C./ Stationary Phase Culture |
|---|---|---|---|---|
| Control | Total | >1000 | Total | >1000 |
| 87° C. | 0 colonies | 0 colonies | 0 colonies | 0 colonies |
| 92° C. | 0 colonies | 0 colonies | 0 colonies | 0 colonies |
| 97° C. | 0 colonies | 0 colonies | 0 colonies | 0 colonies |
| Control | Total | >1000 | Total | >1000 |

The log phase cultures appeared predominantly to contain a single colony type of microorganism. The stationary phase cultures contained a single microorganism colony type and an organism that appeared to be a fungus or a filamentous bacterium.

None of the heated culture samples exhibited significant growth beyond 57° C. The difference in the growth phase of the cultures, i.e., log phase versus stationary phase, did not result in a significant difference in growth. However, the 37° C./Log Phase Culture did appear to exhibit some growth advantage. Note that at 52°, the 37° C./Log Phase Culture still had microbial growth covering the entire plate, whereas the growth of the other samples had been reduced to countable quantities.

In addition, the 37° C./Stationary Phase Culture and 37° C./Log Phase Culture samples exhibited a growth advantage over the 30° C./Stationary Phase Culture and 30° C./Log Phase Culture which is commensurate with the differential initial growth temperature of these samples. That is, because microorganism cultures can be adapted to higher temperatures within limits by slowly raising or lowering the growth temperature, by raising the temperature, the upper and lower limits of growth are both shifted upwards. Thus the 37° samples were amenable to more substantial growth at higher temperatures than the 30° samples.

Along these lines, a new culture of the 37° C./Log Phase Culture was established using minimal medium with TNT. A sample of this culture was placed in a water bath wherein the temperature was raised 1° C. every two days. Significant growth was exhibited as high as 41° C.

EXAMPLE 8

In order to assess the survival characteristics of the microorganism culture during cooling of the explosive charge, the following simulated casting experiment was performed using the 37° C./Log Phase Culture. Small samples of this culture were placed in tubes in water baths at 95° C. and 80° C. These water baths were programmed to drop 1° C. every minute based on a reasonable approximation of the rate of cooling experienced by the charge. At five minute intervals, small samples were removed from the tubes in the water baths and plated on nutrient agar plates. These plates were incubated at 30° C. overnight and checked at 12 and 36 hours for microorganism colonies. After 36 hours the growth on the plates was evaluated. A non-heated sample was included as the control. The results of this study are illustrated in Table 8 below.

The results of this study indicate that the samples from the 80° C. water bath had a better survival rate than the samples from the 95° C. water bath.

TABLE 8

Temperature tolerance of microorganism consortium in simulated casting.

| Temperature | Time | 95° C. Bath | 80° C. Bath |
|---|---|---|---|
| Control | 0 min | Total | Total |
| 90° C. | 5 min | 0 colonies | NA |
| 85° C. | 10 min | 1 colony | NA |
| 80° C. | 15 min | 0 colonies | NA |
| 75° C. | 20 min/5 min | 0 colonies | 1 colony |
| 70° C. | 25 min/10 min | 1 colony | 2 colonies |
| 65° C. | 30 min/15 min | 1 colony | 1 colony |
| 60° C. | 35 min/20 min | 1 colony | 3 colonies |
| 55° C. | 40 min/25 min | 0 colonies | 1 colony |
| 50° C. | 45 min/30 min | 0 colonies | 4 colonies |
| 45° C. | NA/35 min | NA | 3 colonies |
| 40° C. | NA/40 min | NA | 1 colony |
| 35° C. | NA/45 min | NA | 5 colonies |

EXAMPLE 9

The purpose of the following evaluation was to demonstrate that any growth on TNT was greater than that which might be expected from low level contamination by nitrogen from other sources. In order to evaluate the growth characteristics of the microorganism culture with respect to the nitrogen supply, the following experiment was performed under aerobic conditions.

A sample of the 37° C./Log Phase Culture was placed in each of three fresh media formulations. The first contained mineral salts defined medium (MMO) and ammonia as the nitrogen source. The second contained MMO and TNT as the nitrogen source. The third contained only MMO and no added nitrogen. The cultures were then grown and shaken in an incubator at 37° C.

Growth was measured by evaluating the optical density of the culture. Samples removed from each culture were placed in a spectrophotometer and the optical density was measured at a wavelength of 425 nanometers, a wavelength not normally absorbed by molecules produced by the microorganisms. The optical density of the culture samples represents dispersion of the incident beam by the particulate microorganism. The higher the optical density value, the greater the amount of microbial growth. The optical density results are illustrated in Table 9, below.

TABLE 9

Effect of Nitrogen upon growth of microorganism consortium under aerobic conditions.

| Time | Optical Density of Culture in Ammonia Medium | Optical Density of Culture with TNT | Optical Density of Culture Absent Addition of Nitrogen |
|---|---|---|---|
| 0 hours | 0.006 | 0.166 | 0.005 |
| 20 hours | 0.008 | 0.152 | 0.018 |
| 48 Hours | 0.010 | 0.144 | 0.023 |
| 146 Hours | 1.520 | 0.432 | 0.073 |
| Difference Over Background | 1.514 | 0.266 | 0.068 |
| | NA | 3.99 | NA |

The TNT and No Nitrogen cultures were significantly less productive than the ammonia supplemented cultures. Still the TNT supplemented culture values were consistently higher than the No Nitrogen values. This indicates that the cultures were using TNT as the nitrogen source in the TNT supplemented culture.

EXAMPLE 10

Another study, similar to Example 9, above, was performed under anaerobic conditions. A sample of the 37° C./Log Phase Culture was placed in each of three fresh media formulations. The first contained mineral salts defined medium (MMO) and ammonia as the nitrogen source. The second contained MMO and TNT as the nitrogen source. The third contained only MMO and no added nitrogen. The cultures were placed in sealed serum bottles and the atmosphere was replaced with pure Nitrogen. Cultures were incubated without shaking in an incubator at 37° C. The results of this study are illustrated in Table 10, below.

TABLE 10

Effect of Nitrogen upon growth of microorganism consortium under anaerobic conditions.

| Time | Optical Density of Culture in Ammonia Medium | Optical Density of Culture with TNT | Optical Density of Culture Absent Additional Nitrogen |
|---|---|---|---|
| 0 hours | 0.008 | 0.204 | 0.005 |
| 20 hours | 0.012 | 0.218 | 0.009 |
| 48 Hours | 0.017 | 0.268 | 0.007 |
| 146 Hours | 0.482 | 0.272 | 0.019 |
| Difference | 0.474 | 0.068 | 0.014 |
| Over background | NA | 4.88 | NA |

Once again, the TNT and No Nitrogen cultures were significantly less productive than the ammonia supplemented cultures. Still the TNT supplemented culture values were consistently higher than the No Nitrogen values. This indicates that the cultures were using TNT as the nitrogen source in the TNT supplemented culture. Overall, the anaerobic conditions showed less growth than the aerobic cultures.

EXAMPLE 11

In order to evaluate the thermal resistance of the microorganism consortium in a system which will adequately mimic those of a pentolite pour, fresh samples of a TNT grown consortium and a control absent TNT were freeze dried and tested directly for temperature sensitivity. The freeze dried samples were placed into aluminum foil packets. Aluminum foil was used because its heat transference properties ensured that the temperature experienced by the freeze dried powder approximated that produced by the oven. The foil packets were placed in an oven at a starting temperature of either 100° C. or 80° C. The initial 100° C. and 80° C. temperatures were maintained for 2 minutes. Each temperature was then incrementally decreased at the rate of 1° C. per minute to 35° C. The packets remained at 35° C. for 10 minutes and were then removed from the oven. The contents of the packets were placed in MMO with TNT and glycerol, and then placed in a shaking incubator at 37° C. The negative controls were void of any color which indicates complete absence of nitrogen degradation. All other samples were in various stages of TNT degradation as indicated by the color reduction in the samples from colorless to light orange to deep red or violet. The samples that started at 80° C. exhibited more advanced TNT degradation than those that started at 100° C.

These results were in accordance with the results of Example, 8, above. To reiterate, in that study the samples from the 80° C. water bath had a more optimal survival rate that the samples from the 95° C. water bath. Therefore, although the consortium did respond after experiencing temperatures as high as 100° C., a maximum of 80° C. represented the more optimal initial temperature.

The lyophilized microorganisms still produced significant bioremediation results even after being exposed to temperatures corresponding to that of a hot melt of explosive material. Accordingly, it can be concluded that lyophilization of microorganisms dramatically improves the thermal resistance of the microorganisms.

EXAMPLE 12

In order to further evaluate the thermal tolerance and protection of the microorganism consortium, freeze drying was compared with microencapsulation. The microencapsulation procedure required maintaining a substantial amount of fresh cell culture. The cells were divided into 4 samples and resuspended in phosphate buffered saline (PBS); PBS and 3% dried milk; PBS and 3% bentonite clay; and minimal medium with glycerol. Samples of the four suspensions were prepared by freeze drying 2 ml portions. The remainder of the suspensions was divided into 2 samples for encapsulation into alginate and polyacrylamide. Encapsulation into alginate was accomplished by adding sodium alginate to the suspension sample and then adding the mixture dropwise into a Calcium Chloride solution, with a molarity of 0.1. Encapsulation into polyacrylamide was accomplished by combining a biacrylamide mixture with a catalyst, such as a product sold as Temed, and betamercaptoethanol. As the mixture polymerized, the microorganism suspension was trapped in a gel matrix. Half of each sample selected for encapsulation (alginate or polyacrylamide), was freeze dried and the other half was air dried.

All samples, (freeze dried, encapsulated and freeze dried, encapsulated and air dried), were exposed to the temperature curve of Example 8, above. The samples were then added to low temperature agar and overlaid on total nutrient agar. Outgrowth and survival of the samples was evaluated. Additional portions of each sample were then added back to minimal medium with glycerol and TNT to assess the survival of the TNT-critical portions of the consortium.

The encapsulated samples did not result in a significant difference in growth as compared with the freeze dried samples. Thus encapsulation did not offer any distinct advantage over freeze drying with respect to temperature tolerance and subsequent survivability of the microorganism consortium.

EXAMPLE 13

In order to evaluate the thermal resistance of the microorganism consortium in a foam material package, samples of the consortium, in the form of a freeze-dried powder, were packaged into starch "peanuts." The packing material was cored, filled with powder and a portion of the core replaced. The starch structure was not altered at the temperatures tested.

The packets were placed in the oven at a temperature of 100° C. This temperature was maintained for two minutes and then the temperature was decreased at the rate of 1° C. per minute to 35° C. The packets remained at 35° C. for ten minutes and were then removed from the oven. The contents of the packets were placed in MMO/glycerol/TNT and then placed in a shaking incubator at 37° C. Changes were noted based on the color changes noted in other TNT cultures. Optical densities were not feasible because of the added turbidity from both starch and dried milk components of the test systems.

All of the cultures contained in the starch peanuts exhibited a dark reddish color of an advanced TNT culture.

EXAMPLE 14

This experiment was designed to incorporate into mass balance experiments information concerning the effect of nutrient additions to the growth media. These experiments were run using saturated solutions of TNT/PETN. Saturated solutions were prepared as follows:

1. A TNT/PETN saturated solution was prepared by allowing minimal medium (without glycerol) to sit with excess pentolite until TNT levels did not increase further.
2. 100 ml aliquots were then decanted into growth flasks and glycerol was added. The medium to be tested was inoculated with the TNT consortium and samples taken at regular intervals. The results of these experiments on saturated solutions are shown in the following table:

TABLE 14

| Saturated Growth (ppm per sample) | | | |
|---|---|---|---|
| Growth Regime | TNT | PETN | ADNT |
| Control | 47.2 | 11.3 | 110.6 |
|  | 39.7 | 19.2 | 94.9 |
|  | 44.7 | — | 103.8 |
| Glycerol | 18.6 | 50.7 | 121.7 |
|  | 20.3 | 49.9 | 119.0 |
|  | 19.7 | 48.1 | 120.5 |
| MMO/TNT Only | 160.0 | 12.2 | 51.1 |
|  | 161.0 | 19.5 | — |
|  | 171.0 | 14.2 | 51.4 |
| Casamino Acids | 0.00 | 14.9 | 0.00 |
|  | 0.00 | 0.00 | 0.00 |
|  | 0.00 | 0.00 | 0.00 |

Because sterility was not a presupposed starting condition in these trials, it was not surprising to see apparent activity in all conditions. There was observed a general trend in the area of carbon sources, however. It is apparent that some additional carbon source beyond TNT or PETN improves performance of the bioremediating activity of the microorganism.

The present invention may be embodied in other specific forms without departing from the spirit or essential characteristics thereof The described embodiments are to be considered in all respects only as illustrated and not restrictive. The scope of the invention is, therefore, indicated by the appended claims, rather by the foregoing description. All changes which come within the meaning and range of equivalency of the claims are to be embraced within the scope of those claims.

What is claimed is:

1. An explosive capable of self-remediation, if the explosive device fails to detonate, said explosive device comprising:
   a. a quantity of explosive material, said quantity of explosive material being configured in a form capable of detonation;
   b. a carrier disposed proximate to said quantity of explosive material; and
   c. a microorganism capable of bioremediating said quantity of explosive material, said microorganism contained within said carrier and initiating bioremediation of said quantity of explosive material.

2. An explosive device capable of self-remediation; if the explosive device fails to detonate, said explosive device comprising:
   a. a quantity of explosive material, said quantity of explosive material being configured in a form capable of detonation;
   b. a carrier disposed proximate to said quantity of explosive material, said carrier comprising a foam material; and
   c. a microorganism capable of bioremediating said quantity of explosive material, said microorganism contained within said carrier and initiating bioremediation of said quantity of explosive material.

3. An explosive device as recited in claim 2, wherein said foam material further comprises an explosive material.

4. An explosive device as recited in claim 2, wherein said carrier comprises a foamed cellulose.

5. An explosive device as recited in claim 2, wherein said carrier comprises a foamed starch.

6. An explosive device as recited in claim 1, wherein said carrier comprises a nutrient.

7. An explosive device as recited in claim 6, wherein said nutrient comprises a nutrient selected from the group consisting of trace elements, carbon, nitrogen, and phosphate.

8. An explosive device capable of self-remediation, if the explosive device fails to detonate, said explosive device comprising:
   a. a quantity of explosive material, said quantity of explosive material being configured in a form capable of detonation;
   b. a carrier disposed proximate to said quantity of explosive material, said carrier comprising a nutrient, and said nutrient comprising casamino acids;
   c. a microorganism capable of bioremediating said quantity of explosive material, said microorganism contained within said carrier and initiating bioremediation of said quantity of explosive material.

9. An explosive device as recited in claim 1, wherein said carrier further includes cellulose.

10. An explosive device as recited in claim 6, wherein said carrier further includes a binder.

11. An explosive device capable of self-remediation, if the explosive device fails to detonate, said explosive device comprising:
    a. a quantity of explosive material, said quantity of explosive material being configured in a form capable of detonation;
    b. a nutrient intermixed with said quantity of explosive material;
    c. a carrier disposed proximate to said quantity of explosive material; and
    d. a microorganism capable of bioremediating said quantity of explosive material, said microorganism contained within said carrier and initiating bioremediation of said quantity of explosive material.

12. An explosive device as recited in claim 11, wherein said nutrient comprises a nutrient selected from the group consisting of trace elements, carbon, nitrogen, and phosphate.

13. An explosive device capable of self-remediation, if the explosive device fails to detonate, said explosive device comprising:
    a. a quantity of explosive material, said quantity of explosive material being configured in a form capable of detonation and comprising a nutrient; and
    b. a carrier disposed proximate to said quantity of explosive material; and
    c. a microorganism capable of bioremediating said quantity of explosive material, said microorganism contained within said carrier and initiating bioremediation of said quantity of explosive material; and d. wherein said nutrient comprises casamino acids.

14. An explosive device as recited in claim 1, wherein said microorganism is deposited on a surface of said at least one carrier.

15. An explosive device as recited in claim 1, wherein said microorganism comprises a microorganism selected from the group consisting of Pseudomonas spp., Escherichia spp., Morganella spp., Rhodococcus spp., Comamaonas spp., and denitrifying microorganisms.

16. An explosive device as recited in claim 1, wherein said microorganism comprises a microorganism in Pseudomonas spp. selected from the group consisting of aeruginosa, fluorescens, acidovorans, mendocina, and cepacia.

17. An explosive device as recited in claim 1, wherein said microorganism is one of a plurality of types of microorganisms that together define a microorganism consortium.

18. An explosive device as recited in claim 17, wherein said microorganism consortium comprises to the microorganism consortium identified at the American Type Culture Collection by ATCC Designation No. 55784.

19. An explosive as recited in claim 1, wherein said explosive material comprises an explosive material selected from the group consisting of organic nitroaromatic explosives, organic nitramine explosives, and organic nitric ester explosives.

20. An explosive device as recited in claim 1, wherein said explosive material comprises an explosive material selected from the group consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

21. An explosive device as recited in claim 1, wherein said microorganism is mobile and can initiate bioremediation of said quantity of explosive material.

22. An explosive device as recited in claim 1, wherein said carrier is dispersed within said quantity of explosive material.

23. An explosive as recited in claim 1, wherein said explosive device further comprises detonation means, and wherein said carrier surrounds said detonation means.

24. An explosive device as recited in claim 1, wherein said microorganism is dehydrated.

25. An explosive device as recited in claim 1, wherein said microorganism is freeze dried.

26. An explosive device as recited in claim 1, wherein said carrier is sufficiently resistant to heat that a significant portion of said microorganism survives a manufacturing process at a temperature of about 100° C.

27. An explosive device capable of selfremediation, if the explosive device fails to detonate, said explosive device comprising:

a. a quantity of explosive material, said quantity of explosive material being configured in a form capable of detonation;

b. a carrier disposed proximate to said quantity of explosive material;

c. a thermal protection additive included in said carrier; and d. a microorganism capable of bioremediating said quantity of explosive material, said microorganism contained within said carrier and initiating bioremediation of said quantity of explosive material.

28. An explosive device as recited in claim 27, wherein said explosive device further comprises a shell containing said quantity of explosive material, and wherein said shell enables water to flow from the exterior of said shell through said shell into contact with said explosive material.

29. An explosive device as recited in claim 1, wherein said microorganism is freeze dried and reactivated.

30. An explosive device as recited in claim 11, wherein said microorganism comprises a microorganism selected from the group consisting of Pseudomonas spp., Escherichia spp., Morganella spp., Rhodococcus spp., Comamonas spp., and denitrifying microorganisms.

31. An explosive device as recited in claim 11, wherein said microorganism comprises a microorganism in Pseudomonas spp. selected from the group consisting of aeruginosa, fluorescens, acidovorans, mendocina, and cepacia.

32. An explosive device as recited in claim 11, wherein said microorganism is one of a plurality of types of microorganisms that together define a microorganism consortium.

33. An explosive device as recited in claim 32, wherein said microorganism consortium comprises to the microorganism consortium identified at the American Type Culture Collection by ATCC Designation No. 55784.

34. An explosive device as recited in claim 11, wherein said explosive material comprises an explosive material selected from the group consisting of organic nitroaromatic explosives, organic nitramine explosives, and organic nitric ester explosives.

35. An explosive device as recited in claim 11, wherein said explosive material comprises an explosive material selected from the group consisting of trinitrotoluene, hexanitrostilbene, hexanitroazobenzene, diaminotrinitrobenzene, triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

36. An explosive device as recited in claim 11, wherein said microorganism is mobile and can initiate bioremediation of said quantity of explosive material.

37. An explosive device as recited in claim 11, wherein said microorganism is dehydrated.

38. An explosive device as recited in claim 11, wherein said microorganism is freeze dried.

39. An explosive device as recited in claim 11, wherein said microorganism is sufficiently resistant to heat so that a significant portion of a plurality of said microorganisms survives a placement process at a temperature of about 100° C.

40. An explosive device as recited in claim 11, wherein said explosive further comprises a shell containing said quantity of explosive material, said shell enabling water to flow from the exterior thereofthrough said shell into contact with said quantity of explosive material.

41. An explosive device as recited in claim 1, wherein said microorganism is in an aggregation with other microorganisms.

42. An explosive device as recited in claim 1, wherein said explosive material comprises an inorganic nitrate explosive.

43. An explosive device as recited in claim 1, wherein said explosive material comprises ammonium nitrate.

44. An explosive device as recited in claim 11, wherein said explosive material comprises an inorganic nitrate explosive.

45. An explosive device as recited in claim 11, wherein said explosive material comprises ammonium nitrate.

* * * * *

UNITED STATES PATENT AND TRADEMARK OFFICE
CERTIFICATE OF CORRECTION

PATENT NO. : 6,334,395 B1
DATED : January 1, 2002
INVENTOR(S) : Farrell G. Badger, Brendan M. Welch, Ronald D. Thomas, Lyman G. Bahr and Dean F. Richards It is certified that error appears in the above-identified patent and that said Letters Patent is hereby corrected as shown below:

Title page,
Item [75], the "Inventors", change "Farmington, CT" to -- Uxbridge, MA --, change "Woodlands" to -- Woodland --
Item [56], References Cited, under U.S. PATENT DOCUMENTS,
Insert -- 4,044,684   8/1977   Gaggini et al.…...102/90 --
Insert -- 5,593,888   1/1997   Glaze et al.…..435/262.5 --
Insert -- 5,711,020   1/1998   Wolfe et al.……588/203 --
Item [56], References Cited, insert -- FOREIGN PATENT DOCUMENTS
512,660   11/1992   Europe        A62D   3/00 --
Under OTHER PUBLICATIONS,
Change "punds," to -- pounds, --

Column 1,
Line 20, change "As" to -- as --
Line 21, change "application" ($2^{nd}$ occurrence) to -- applications --
Line 37, after "which" insert -- , --
Line 56, change "risks" to -- risk --

Column 2,
Line 51, change "are" to -- is --

Column 4,
Line 12, change "are" to -- is --
Line 33, after "that" and "removed" insert -- , --
Line 38, change "include" to -- includes --
Lines 58-59, delete "can be characterized in that the microorganisms"

Column 6,
Line 17, delete "and"

Column 7,
Line 36, change "fmal" to -- final --

Column 8,
Line 12, delete "of the"

Column 9,
Line 12, after "55784" insert -- , --
Line 38, after "current" change "system" to -- invention --
Line 62, change "design," to -- design and --

UNITED STATES PATENT AND TRADEMARK OFFICE
CERTIFICATE OF CORRECTION

PATENT NO.    : 6,334,395 B1
DATED         : January 1, 2002
INVENTOR(S)   : Farrell G. Badger, Brendan M. Welch, Ronald D. Thomas, Lyman G. Bahr and Dean F. Richards It is certified that error appears in the above-identified patent and that said Letters Patent is Column 10,
Line 33, after "may" and "example" insert -- , --
Line 52, change "C." to -- C., --

Column 11,
Line 9, after "than" delete "a"
Line 10, change "microorganism" to -- microorganisms --
Line 21, after "destroyed" insert -- , --
Line 29, after "thin layers" and "cool", insert -- , --

Column 12,
Line 7, after "the nutrient" insert -- , --
Line 9, after "milk" change ";" to -- , --
Line 15, after "milk," insert -- and --
Line 34, change "microorganism" to -- microorganisms --

Column 13,
Line 55, change "chips 30" to -- chips 60 --
Line 56, change "aides" to -- aids --

Column 14,
Line 23, change "reduce" to -- reduces --

Column 15,
Line 4, after "which" insert -- , --
Line 44, after "moist" insert -- , --
Lines 61-62, change "condition" to -- conditions --

Column 16,
Line 16, after "material 30" insert -- , --
Line 28, change "are" to -- is a --
Line 29, change "examples" to -- example --
Line 51, change "FIG." to -- FIGS. --
Line 60, after "shell 22" insert -- , --

Column 17,
Line 3, change "material." to -- material 30. --

UNITED STATES PATENT AND TRADEMARK OFFICE
CERTIFICATE OF CORRECTION

PATENT NO.    : 6,334,395 B1
DATED         : January 1, 2002
INVENTOR(S)   : Farrell G. Badger, Brendan M. Welch, Ronald D. Thomas, Lyman G. Bahr and Dean F. Richards It is certified that error appears in the above-identified patent and that said Letters Patent is Column 18,
Line 17, after "were split" insert -- , --
Line 64, after "time" insert -- , --

Column 19,
Line 5, after "insufficient" insert -- , --
Line 27, after "below" insert -- , --

Column 20,
Line 15, change "mediur" to -- medium --
Line 45, change after ""B"" insert -- , --

Column 22,
Line 53, change "Cultere" to -- Culture --

Column 23,
Line 13, change "ofthis" to -- of this --
Line 65, after "Example" delete "," and after "study" insert -- , --
Line 67, change "that" to -- than --

Column 24,
Line 32, after "polyacrylamide)" delete ","
Line 34, after "samples" delete ","
Line 35, after "dried)" delete ","
Line 38, change "was" to -- were --

Column 25,
Line 6, change "experiments" to -- experiment --
Line 45, after "thereof" insert -- . --
Line 48, after "rather" insert -- than --
Line 65, change ";" to -- , --

UNITED STATES PATENT AND TRADEMARK OFFICE
CERTIFICATE OF CORRECTION

PATENT NO. : 6,334,395 B1
DATED : January 1, 2002
INVENTOR(S) : Farrell G. Badger, Brendan M. Welch, Ronald D. Thomas, Lyman G. Bahr and Dean F. Richards It is certified that error appears in the above-identified patent and that said Letters Patent is Column 27,
Line 5, delete "at least one"
Line 20, after "comprises" delete "to"
Line 43, after "explosive" insert -- device --
Line 54, change "selfremediation," to -- self-remediation, --

Column 28,
Line 22, after "comprises" delete "to"
Line 52, after "explosive" insert -- device --
Line 54, change "thereofthrough" to -- thereof through --

Signed and Sealed this

Sixteenth Day of July, 2002

Attest:

JAMES E. ROGAN
*Attesting Officer*                *Director of the United States Patent and Trademark Office*